US011317848B2

(12) United States Patent
Lazarini-Serandour et al.

(10) Patent No.: US 11,317,848 B2
(45) Date of Patent: May 3, 2022

(54) OLFACTORY MEANS FOR THE DIAGNOSIS OF NEUROLOGICAL COMPLICATIONS OF NERVOUS SYSTEM INFECTION

(71) Applicants: INSTITUT PASTEUR, Paris (FR); CENTRE NATIONAL DE LA RECHERCHE SCIENTIFIQUE, Paris (FR); ASSISTANCE PUBLIQUE—HOPITAUX DE PARIS, Paris (FR)

(72) Inventors: Françoise Lazarini-Serandour, Paris (FR); Pierre-Marie Lledo, Antony (FR); Natacha Teissier, Senlis (FR); Sarah Levivien, Levallois-Perret (FR)

(73) Assignees: INSTITUT PASTEUR, Paris (FR); CENTRE NATIONAL DE LA RECHERCHE SCIENTIFIQUE, Paris (FR); ASSISTANCE PUBLIQUE—HOPITAUX DE PARIS, Paris (FR)

( * ) Notice: Subject to any disclaimer, the term of this patent is extended or adjusted under 35 U.S.C. 154(b) by 0 days.

(21) Appl. No.: 16/302,387

(22) PCT Filed: May 19, 2017

(86) PCT No.: PCT/EP2017/062097
§ 371 (c)(1),
(2) Date: Nov. 16, 2018

(87) PCT Pub. No.: WO2017/198816
PCT Pub. Date: Nov. 23, 2017

(65) Prior Publication Data
US 2020/0121239 A1  Apr. 23, 2020

(30) Foreign Application Priority Data
May 20, 2016  (EP) .................................... 16305584

(51) Int. Cl.
A61B 5/04 (2006.01)
A61B 5/00 (2006.01)
A61K 49/00 (2006.01)

(52) U.S. Cl.
CPC .......... *A61B 5/4011* (2013.01); *A61B 5/4082* (2013.01); *A61B 5/4088* (2013.01); *A61K 49/00* (2013.01)

(58) Field of Classification Search
CPC ... A61B 5/4011; A61B 5/4082; A61B 5/4088; A61B 5/4017; A61K 49/00; A61M 2021/0016; G01N 33/48
See application file for complete search history.

(56) References Cited

U.S. PATENT DOCUMENTS 6,957,038 B1    10/2005  Gartner
2007/0077204 A1  4/2007  Devanand et al.
(Continued)

FOREIGN PATENT DOCUMENTS

FR         2122453 A      9/1972
WO    WO-2014170206 A1 * 10/2014  ............. A61B 5/165
WO       2016/007817 A1    1/2016

OTHER PUBLICATIONS

European Search Report, Application No. EP 16305584, dated Nov. 24, 2016.
(Continued)

*Primary Examiner* — Ankit D Tejani
*Assistant Examiner* — Joshua Brendon Solomon
(74) *Attorney, Agent, or Firm* — Arrigo, Lee, Guttman & Mouta-Bellum LLP

(57) ABSTRACT

The application generally relates to olfaction as a biomarker, more particularly as a prognostic biomarker or biological predictor, of neurosensory disease or disorder and/or of neurocognitive disease or disorder, in subjects whose ner-
(Continued)

vous system has been infected by an infectious agent, such as by a neurotropic virus, bacterium, protozoan parasite, fungus or prion, more particularly by a neurotropic virus.

19 Claims, 9 Drawing Sheets

(56) References Cited

U.S. PATENT DOCUMENTS

| | | | |
|---|---|---|---|
| 2007/0092889 A1* | 4/2007 | Cox | C12Q 1/6883 435/6.16 |
| 2014/0155271 A1* | 6/2014 | Hatchwell | C12Q 1/6809 506/2 |
| 2016/0073944 A1* | 3/2016 | Lazarini | A61P 25/24 600/303 |

OTHER PUBLICATIONS

International Search Report, Application No. PCT/EP2017/062097, dated Aug. 21, 2017.
Pollatos et al: "Reduced olfactory sensitivity in subjects with depressive symptoms", Journal of Affective Disorders, Elsevier Biochemical Press, Amsterdam, NL, vol. 102, No. 1-3, Jul. 12, 2007 (Jul. 12, 2007), pp. 101-108.
Laing D G et al: "Quality and intensity of binary odor mixtures", Physiology and Behavior, Elsevier Science Ltd., Oxford, GB, vol. 33, No. 2, Aug. 1, 1984 (Aug. 1, 1984) pp. 309-319.
T. Hummel et al: "'Sniffin' Sticks': Olfactory Performance Assessed by the Combined Testing of Odour Identification, Odor Discrimination and Olfactory Threshold", Chemical Senses, vol. 22. No. 1, Jan. 1, 1997 (Jan. 1, 1997). pp. 39-52.
Helen E. Farrell et al: "Murine Cytomegalovirus Exploits Olfaction to Enter New Hosts", MBIO, vol. 7, No. 2, May 4, 2016 (May 4, 2016), pp. e00251-16.
Kollndorfer K et al: "Effects of chronic peripheral olfactory loss on functional brain networks" Neuroscience vol. 310, Dec. 3, 2015 (Dec. 3, 2015), pp. 589-599.
Hummel Thomas et al: "Volume of olfactory bulb and depth of olfactory sulcus in 378 consecutive patients with olfactory loss", Journal of Neurology—Zeitschrift Fuer Neurologie, Springer Verlag, Berlin, DE, vol. 262. No. 4, Feb. 26, 2015 (Feb. 26, 2015), pp. 1046-1051.
Basile Nicolas Landis et al: "Olfactory dysfunction following herpetic meningoencephalitis", Journal of Neurology, Steinkopff-Verlag, DA, vol. 257. No. 3. Oct. 10, 2009 (Oct. 10, 2009), pp. 439-443.
Philippe Rombaux et al: "Usefulness and feasibility of psychophysical and electrophysiological olfactory testing in the rhinology clinic", Rhinology, vol. 47, No. 1, Mar. 1, 2009 (Mar. 1, 2009), pp. 28-35.
Masato Suzuki et al: "Deciphering the Receptor Repertoire Encoding Specific Odorants by Time-Lapse Single-Cell Array Cytometry", Scientific Reports, vol. 6, No. 1, Feb. 2, 2016 (Feb. 2, 2016).

* cited by examiner

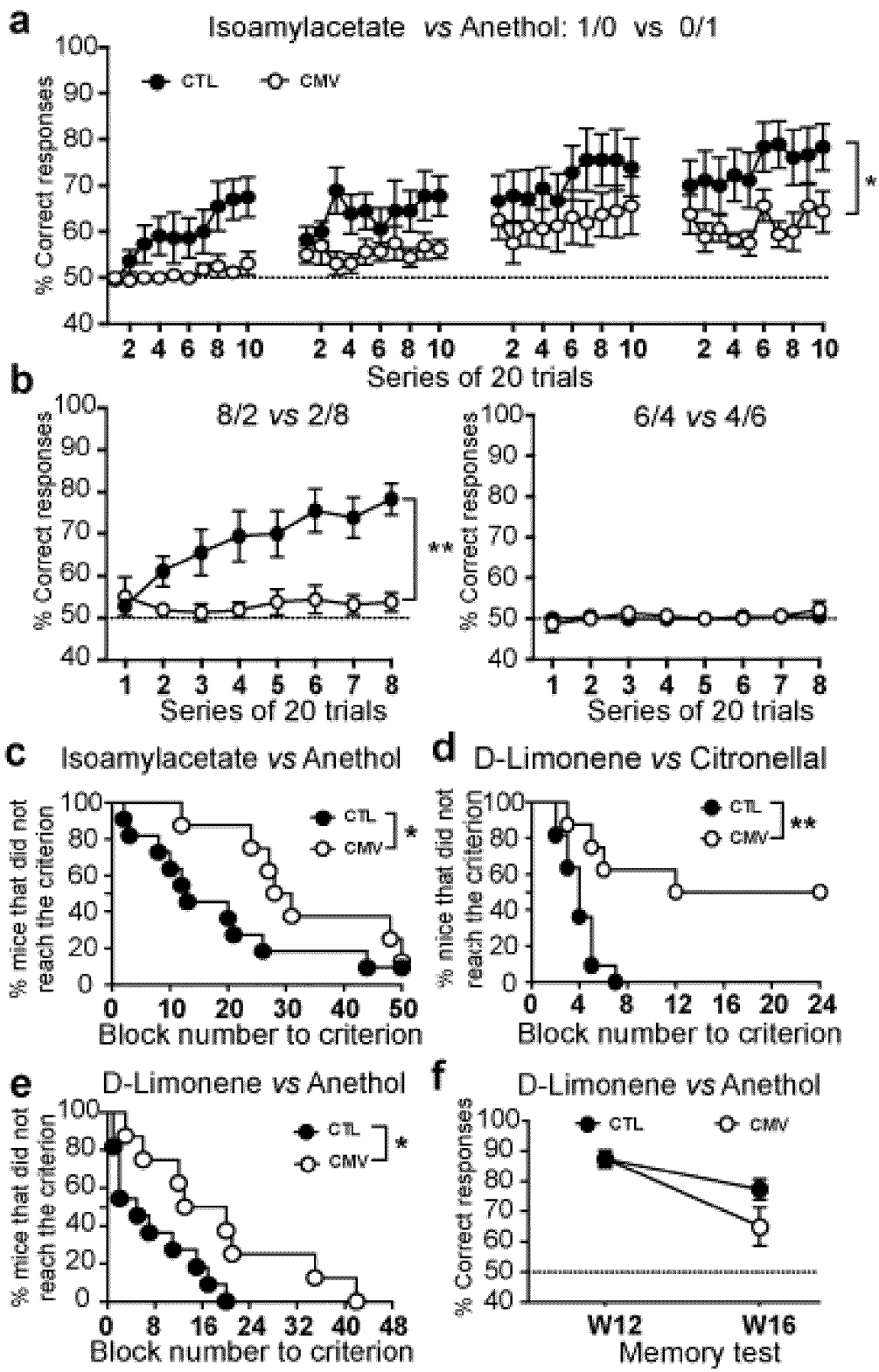
FIGURE 3 (1)

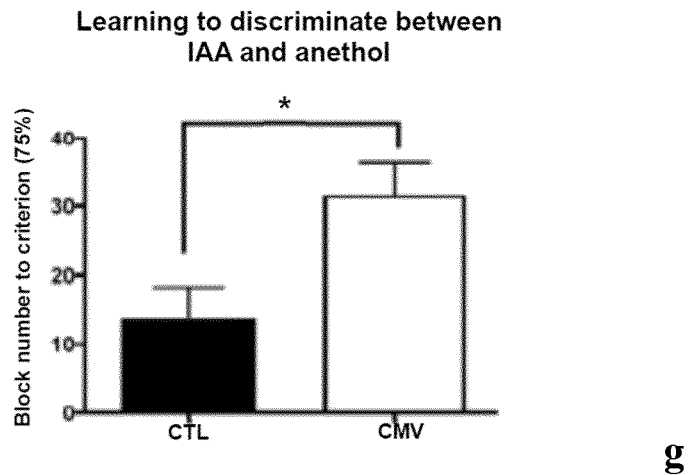
g
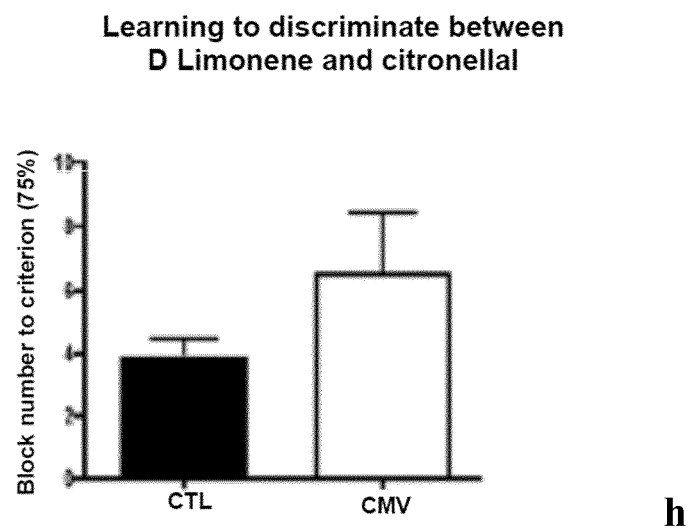
h
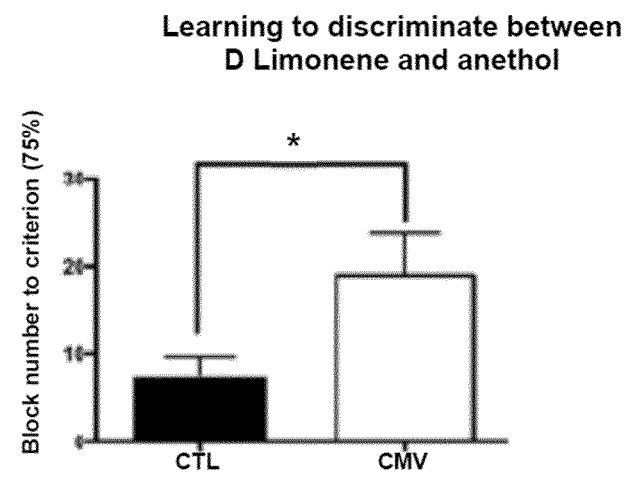
i
FIGURE 3 (2)

OLFACTORY MEANS FOR THE DIAGNOSIS OF NEUROLOGICAL COMPLICATIONS OF NERVOUS SYSTEM INFECTION

FIELD

The application relates to olfactory means involving odorants mixed at different proportions, and to the use of these olfactory means to determine the olfactory discrimination capacity of a subject, who has an infection of his/her nervous system. According to the application, a decrease in the olfactory discrimination capacity of these subjects, as measured by these olfactory means, is indicative of the development of neurological complications, e.g., the development of central or peripheral neuropathies, hearing loss, mental retardation, language retardation, psychomotor retardation or visual loss.

The means of the application enable the diagnosis of neurological complications of nervous system infection, more particularly the early diagnosis of neurological impairment in a subject, who has an infection of his/her nervous system. The means of the application notably allow for an early application of medical treatment to counter-act the infection and/or the neurological impairment, as well as for an optimized monitoring of the medical treatment.

BACKGROUND

Infectious agents that infect the nervous system, i.e., the Central Nervous System (CNS) and/or the Peripheral Nervous System (PNS), notably include neurotropic virus, bacterium, protozoan parasite, fungus or prion. Infection of the nervous system may lead to neurological impairment, e.g., to neurodegeneration, which in turn may result in a neurosensory or neurocognitive disease or disorder. The progression of neurological impairment is not necessarily linear over time, and may even start a long time after infection has occurred.

The nature of the infectious agents is relatively diverse and includes bacteria, protozoan parasites, fungi, viruses and prions. For example, Zika virus (ZIKV) and congenital CytoMegalovirus (CMV) are major public health concerns due to severe sequelae in the fetus and newborn.

During the Epidemic of ZIKV in French Polynesia, the frequency of microcephaly in fetuses and neonates from ZIKV-infected mothers was about 1%. Moreover, severe neurological complications such as Guillain-Barré syndrome were found following ZIKV infection in adults.

Herpes virus type 5 or human cytomegalovirus (HCMV) is an opportunist pathogen which is the first cause of congenital cerebral malformation induced by viral infection, mental retardation and nongenetic sensorineural hearing loss (SNHL). In France, 1% of newborns are HCMV infected. 10-15% of newborns with congenital CMV infection have symptomatic disease and are at high risk of developing adverse long-term outcomes, such as neurologic and sensorineural handicaps including visual, auditory or vestibular lesions. Conversely, amongst asymptomatic CMV-infected newborns, about 10-15% of them develop long-term sequelae, such as SNHL. Hearing loss in congenital CMV infected children can appear neonataly but can also occur later in childhood, is often progressive and requires ongoing audiologic evaluation. The hearing may in some rare cases improve, be fluctuating or more frequently deteriorate. It is difficult to predict the consequences of HCMV infection because of a large gap in the knowledge of viral pathogenesis and immunology. The unique species reservoir of HCMV is human. HCMV infection is characterized by persistence of the virus in infected hosts for the lifespan. HCMV can reactivate in certain contexts such as immunodeficiency, immunosuppression or some chronic diseases, and then give rise to recurrent disease. Endothelial cells and cells of the myeloid lineage are considered to form the main reservoir for latent HCMV genomes. While there is no neurologic symptom in immunocompetent infected hosts when HCMV primary infection occurs after birth, congenital HCMV often leads to brain dysfunction. After maternal placental transmission, HCMV invades the peripheral and central nervous system (CNS) of the fetus. It targets the stria vascularis of the cochlea, the mammalian auditory sensory organ, and the periventricular region of the brain. Innate and adaptive immune responses against HCMV infection are present, including lymphocyte recruitment and activation of microglia, but the immune reaction is limited during fetal life in coping with this virus and protecting brain from neurological damage. The occurrence of long-term outcomes, with delayed onset, might be due to reactivation of HCMV within brain structures.

The application provides olfactory means that enable to diagnose or predict neurological complications of nervous system infection.

SUMMARY

The application generally relates to olfaction, more particularly to olfaction discrimination capacity, and to neurological impairment of subjects, who have been infected by a neurotropic infectious agent.

According to the application, olfaction, more particularly olfaction discrimination capacity, can be a biomarker, more particularly a prognostic biomarker (or biological predictor), of neurosensory disease or disorder and/or of neurocognitive disease or disorder, in subjects whose nervous system has been infected by a neurotropic infectious agent.

According to the application, appropriate olfactory means to achieve this result involve odorants mixed at different proportions, and their use to determine the olfactory discrimination capacity of said subjects.

The nervous system can be the Central Nervous System (CNS) and/or of the Peripheral Nervous System (PNS), more particularly the CNS. The infection can be a congenitally-acquired infection.

The application relates more particularly to a kit, which comprises
    a first composition comprising odorants, wherein the odorants of said first composition consist of at least two different odorants, and, separately or distinctly from said first composition,
    a second composition comprising odorants, wherein the odorants of said second composition consist of at least two different odorants, and, separately or distinctly from said first composition and from said second composition,
    a third composition comprising odorants, wherein the odorants of said third composition consist of at least two different odorants,
    wherein the odorants of said second composition are the same compounds as the odorants of said third composition,
    wherein the proportion of the odorants with respect to each other in said second composition is identical to their proportion in said third composition,
    wherein the odorants of said first composition are the same compounds as the odorants of said second composition and as the odorants of said third composition, wherein the proportion of the odorants with respect to each other in said first composition is different from their proportion in said second composition and in said third composition. Said kit is notably suitable for use in the in vivo diagnosis of neurological impairment in a subject, whose nervous system has been infected by a neurotropic infectious agent.

Said use advantageously comprises the sequential smelling or sniffing of said first composition, of said second composition and of said third composition by said subject. Said kit notably allows detecting impairment of the olfactory capacity of said subject to discriminate said first composition from said second and third compositions.

Impairment of the olfactory capacity of said subject to discriminate said first composition from said second and third compositions is a biomarker or biological predictor of neurological impairment in said infected subject.

Also encompassed in the invention is thus a first composition comprising odorants, wherein the odorants of said first composition consist of at least two different odorants, for use in the in vivo diagnosis of neurological impairment in a subject, whose nervous system has been infected by a neurotropic infectious agent, wherein said use comprises:
  separately or distinctly from said first composition, using a second composition comprising odorants, wherein the odorants of said second composition consist of at least two different odorants, and,
  separately or distinctly from said first composition and from said second composition, using a third composition comprising odorants, wherein the odorants of said third composition consist of at least two different odorants,
wherein the odorants of said second composition are the same compounds as the odorants of said third composition,
  wherein the proportion of the odorants with respect to each other in said second composition is identical to their proportion in said third composition,
  wherein the odorants of said first composition are the same compounds as the odorants of said second composition and as the odorants of said third composition,
  wherein the proportion of the odorants with respect to each other in said first composition is different from their proportion in said second composition and in said third composition, and,
  wherein said use comprises the sequential smelling or sniffing of said first composition, of said second composition and of said third composition by said subject.

According to an alternative embodiment the invention relates to:
  a first composition comprising odorants, wherein the odorants of said first composition consist of at least two different odorants, and separately or distinctly from said first composition, a second composition comprising odorants, wherein the odorants of said second composition consist of at least two different odorants, for use in the in vivo diagnosis of neurological impairment in a subject, whose nervous system has been infected by a neurotropic infectious agent, wherein said use comprises
  separately or distinctly from said first composition and from said second composition, using a third composition comprising odorants, wherein the odorants of said third composition consist of at least two different odorants, wherein the odorants of said second composition are the same compounds as the odorants of said third composition,
  wherein the proportion of the odorants with respect to each other in said second composition is identical to their proportion in said third composition,
  wherein the odorants of said first composition are the same compounds as the odorants of said second composition and as the odorants of said third composition,
  wherein the proportion of the odorants with respect to each other in said first composition is different from their proportion in said second composition and in said third composition, and, wherein said use comprises the sequential smelling or sniffing of said first composition, of said second composition and of said third composition by said subject.

In addition, the invention relates to:
  a first composition comprising odorants, wherein the odorants of said first composition consist of at least two different odorants,
  and, separately or distinctly from said first composition,
  a second composition comprising odorants, wherein the odorants of said second composition consist of at least two different odorants, and, separately or distinctly from said first composition and from said second composition,
  a third composition comprising odorants, wherein the odorants of said third composition consist of at least two different odorants,
  wherein the odorants of said second composition are the same compounds as the odorants of said third composition,
  wherein the proportion of the odorants with respect to each other in said second composition is identical to their proportion in said third composition,
  wherein the odorants of said first composition are the same compounds as the odorants of said second composition and as the odorants of said third composition,
  wherein the proportion of the odorants with respect to each other in said first composition is different from their proportion in said second composition and in said third composition, for use in the in vivo diagnosis of neurological impairment in a subject, whose nervous system has been infected by a neurotropic infectious agent, wherein said use comprises the sequential smelling or sniffing of said first composition, of said second composition and of said third composition by said subject.

BRIEF DESCRIPTION OF THE FIGURES

Some of the figures, to which the application refers, are in color(s). The application as filed contains the color print-out of the figures, which can therefore be accessed by inspection of the file of the application at the patent office.

FIG. 3. Effects of CMV congenital infection on olfactory learning and memory. a, b, Graph depicting the percentage of correct responses in each block of the easy (a) discrimination task between Isoamylacetate (S+) and Anethol (S−) or the difficult (b) discrimination tasks between their binary mixtures. The mixture ratio of isoamylacetate and anethol is indicated on the graph. c-e, and g-i % of mice that did not reach the performance criterion for the discrimination task between isoamylacetate and anethol (c,g), D-Limonene and Citronellal (d,h), D-Limonene and Anethol (e,i). f, Long-term memory test. To assess olfactory memory, mice were trained during 5 consecutive days to recall distinguishing D-Limonene and Anethol. Mice were then retested at W16 following the end of the training session (W12). In a, b, f, a score of 50% corresponds to the success rate expected on the basis of chance alone (dashed line). Results in a, b, f are expressed as the mean±s.e.m. of correct response. P values are calculated by two-way analysis of variance (ANOVA) with repeated measures (a, b, 0 or Gehan-Breslow-Wilcoxon test (c-e).

DETAILED DESCRIPTION

Figure 1:
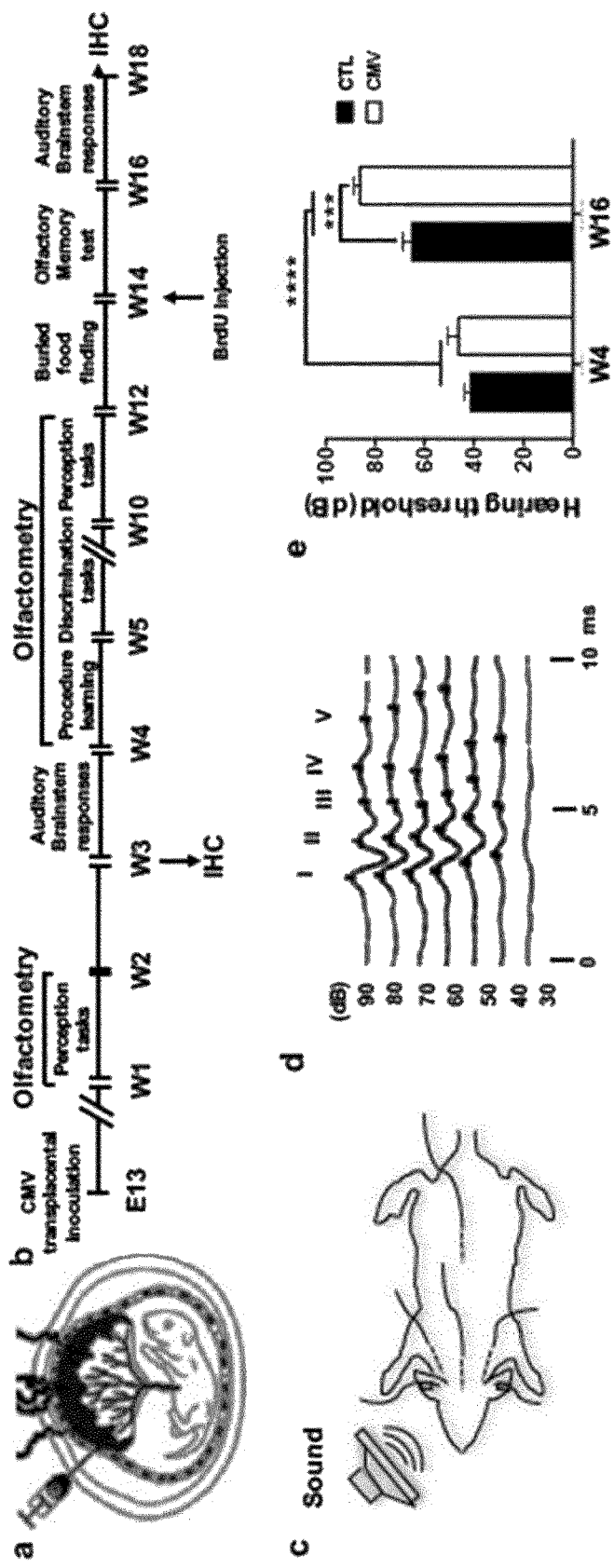
FIG. 1. Impact of CMV congenital infection on hearing. a, Animal model of CMV infection in pregnancy. Murine CMV (Smith strain) or PBS was intraplacentally inoculated in each embryo of pregnant Oncins France 1 (OF1) mice under deep anesthesia. b, Timetable of the experiments. Mice were infected with CMV at E13. Eight CMV-infected male mice, 2 sham mice that received PBS and 9 control male mice of the same age were analyzed using olfactometers and with buried food-finding tests. Their auditory brain stem responses (ABR) were recorded at the end of the procedure. The results of the 2 sham mice have been pooled with the results of 9 control mice. (E, stands for embryonic and W for week). c, ABR recording system in an anesthetized mouse. d, Typical ABR traces depicting waves I-V. e, ABR hearing thresholds for a click (lowest intensity for detection of the wave IV). n=8 male mice per group. P value is calculated by Sidak's multiple comparison test. ***$P<0.001$; mean±s.e.m. in bar graphs.

The invention relates to the subject-matter as defined in the claims as filed and as herein described as the application or invention.

In the application, unless specified otherwise or unless a context dictates otherwise, all the terms have their ordinary meaning in the relevant field(s).

The application generally relates to olfaction, more particularly to olfaction discrimination capacity, as a biomarker, more particularly as a prognostic biomarker (or biological predictor), of neurosensory disease or disorder and/or of neurocognitive disease or disorder, in subjects, who have been infected by a neurotropic infectious agent.

The olfactory means of the application involve odorants mixed at different proportions, and their use to determine the olfactory discrimination capacity of said subjects.

Impairment of the olfactory discrimination capacity as detected by the olfactory means of the application is a biomarker or biological predictor of neurological impairment in a subject, who has been infected by a neurotropic infectious agent.

The application relates to a kit, which comprises compositions comprising (at least two) odorants, as well as to a series or (functional) association of compositions comprising said odorant compositions. The term composition encompasses the meaning of mixture. Therefore, the kit, series, or (functional) association or (use of compositions) comprises several compositions (or using compositions) comprising the same (at least two) odorants, wherein each of said several compositions contain the same (at least two different) odorants, and wherein at least one of said several compositions differs from the other compositions by the proportion in which said (at least two different) odorants are contained.

The kit, series, compositions or (functional) association or use may accordingly comprise
  a first composition comprising odorants, wherein the odorants of said first composition consist of at least two different odorants, and, separately or distinctly from said first composition,
  a second composition comprising odorants, wherein the odorants of said second composition consist of at least two different odorants,
wherein the odorants of said first composition are the same compounds as the odorants of said second composition, and
wherein the proportion of the odorants with respect to each other in said first composition is different from their proportion in said second composition.

The kit, series, compositions or association or use may advantageously comprise
  a first composition comprising odorants, wherein the odorants of said first composition consist of at least two different odorants, and, separately or distinctly from said first composition,
  a second composition comprising odorants, wherein the odorants of said second composition consist of at least two different odorants, and, separately or distinctly from said first composition and from said second composition,
  a third composition comprising odorants, wherein the odorants of said third composition consist of at least two different odorants.

The odorants of said second composition are the same compounds as the odorants of said third composition, and the proportion of the odorants with respect to each other in said second composition is identical to their proportion in said third composition. The third composition advantageously is a duplicate of (i.e., is identical to) said second composition. The odorants of said first composition are the same compounds as the odorants of said second composition and as the odorants of said third composition, and the proportion of the odorants with respect to each other in said first composition is different from their proportion in said second composition and in said third composition.

Also provided herein are the above defined compositions for use in the manufacture of a kit or of a functional assembly for the in vivo diagnosis of neurological impairment in a subject, whose nervous system has been infected by a neurotropic infectious agent.

Also encompassed in the invention is thus a first composition comprising odorants, wherein the odorants of said first composition consist of at least two different odorants, for use in the in vivo diagnosis of neurological impairment in a subject, whose nervous system has been infected by a neurotropic infectious agent, wherein said use comprises
  separately or distinctly from said first composition, using a second composition comprising odorants, wherein the odorants of said second composition consist of at least two different odorants, and,
  separately or distinctly from said first composition and from said second composition, using a third composition comprising odorants, wherein the odorants of said third composition consist of at least two different odorants,
wherein the odorants of said second composition are the same compounds as the odorants of said third composition,
wherein the proportion of the odorants with respect to each other in said second composition is identical to their proportion in said third composition,
wherein the odorants of said first composition are the same compounds as the odorants of said second composition and as the odorants of said third composition, wherein the proportion of the odorants with respect to each other in said first composition is different from their proportion in said second composition and in said third composition, and,
  wherein said use comprises the sequential smelling or sniffing of said first composition, of said second composition and of said third composition by said subject.

According to an alternative embodiment the invention relates to:
  a first composition comprising odorants, wherein the odorants of said first composition consist of at least two different odorants, and separately or distinctly from said first composition, a second composition comprising odorants, wherein the odorants of said second composition consist of at least two different odorants, for use in the in vivo diagnosis of neurological impairment in a subject, whose nervous system has been infected by a neurotropic infectious agent, wherein said use comprises
  separately or distinctly from said first composition and from said second composition, using a third composition comprising odorants, wherein the odorants of said third composition consist of at least two different odorants,
wherein the odorants of said second composition are the same compounds as the odorants of said third composition,
wherein the proportion of the odorants with respect to each other in said second composition is identical to their proportion in said third composition, wherein the odorants of said first composition are the same compounds as the odorants of said second composition and as the odorants of said third composition,
wherein the proportion of the odorants with respect to each other in said first composition is different from their proportion in said second composition and in said third composition, and,
  wherein said use comprises the sequential smelling or sniffing of said first composition, of said second composition and of said third composition by said subject.

In addition, the invention relates to:
  a first composition comprising odorants, wherein the odorants of said first composition consist of at least two different odorants,
  and, separately or distinctly from said first composition, a second composition comprising odorants, wherein the odorants of said second composition consist of at least two different odorants, and, separately or distinctly from said first composition and from said second composition, a third composition comprising odorants, wherein the odorants of said third composition consist of at least two different odorants, wherein the odorants of said second composition are the same compounds as the odorants of said third composition, wherein the proportion of the odorants with respect to each other in said second composition is identical to their proportion in said third composition, wherein the odorants of said first composition are the same compounds as the odorants of said second composition and as the odorants of said third composition, wherein the proportion of the odorants with respect to each other in said first composition is different from their proportion in said second composition and in said third composition, for use in the in vivo diagnosis of neurological impairment in a subject, whose nervous system has been infected by a neurotropic infectious agent, wherein said use comprises the sequential smelling or sniffing of said first composition, of said second composition and of said third composition by said subject.

According to the use for the diagnosis according to the invention, the alteration of the olfactory sensitivity is detected in a subject and said alteration may encompass alteration of the detection threshold for the assayed odorants, alteration of the discrimination of the odorants or alteration of the learning in distinguishing the odorants or a combination of these types of alternation.

According to the invention alteration in olfactory sensitivity is thus a marker of neurological impairment in a subject whose nervous system has been infected by a neurotropic infectious agent. This alteration is detected as a result of the in vivo assay performed on the subject with the disclosed at least three compositions. In a particular embodiment said subject is a subject who is known or detected to have no psychiatric disorder or disease involving mood depression. In a particular embodiment, said subject has been detected positive for infection or likely infection with a neuronal infectious agent, for example with a virus such as CMV (or HCMV) or ZIKV.

Also provided herein is a method for in vivo diagnosis of neurological impairment in a subject, whose nervous system has been infected by a neurotropic infectious agent, wherein said method comprises having the subject perform the sequential smelling or sniffing of a first composition, of a second composition and of a third composition. wherein:

said first composition comprises odorants, wherein the odorants of said first composition consist of at least two different odorants, and said second composition is separate or distinct from said first composition and comprises odorants, wherein the odorants of said second composition consist of at least two different odorants, and, said a third composition is separate or distinct from said first composition and from said second composition and comprises odorants, wherein the odorants of said third composition consist of at least two different odorants, wherein the odorants of said second composition are the same compounds as the odorants of said third composition, wherein the proportion of the odorants with respect to each other in said second composition is identical to their proportion in said third composition, wherein the odorants of said first composition are the same compounds as the odorants of said second composition and as the odorants of said third composition, and wherein the proportion of the odorants with respect to each other in said first composition is different from their proportion in said second composition and in said third composition. Advantageously, the first composition is a composition, which is consciously perceived by smelling or sniffing as different from said second composition, or from said second and third compositions, by a control subject (e.g., a control human being), who is normosmic and who is not infected by a neurotropic infectious agent, i.e., a healthy normosmic control subject.

In other words, the difference in odorant proportion in said first composition compared to said second composition, or compared to said second and third compositions, is sufficient for said first composition to be consciously perceived as different from said second composition, or from said second and third compositions, by a healthy normosmic control subject (e.g., a healthy normosmic human being), who sequentially smells or sniffs each of said odorant compositions.

The kit, series, first, second and third compositions or (functional) association advantageously is (are) for use in the in vivo diagnosis of neurological impairment, in a subject, who has been infected by a neurotropic infectious agent, more particularly in a subject, whose nervous system has been infected by a (neurotropic) infectious agent.

The term neurological impairment is intended in accordance with its ordinary meaning in the field, and encompasses any neurological deficiency. The term neurological impairment encompasses more particularly neurological disability. The term neurological impairment encompasses more particularly neurological disease or disorder, including the early (asymptomatic or symptomatic) stages of neurological disease or disorder.

Said neurological impairment is a neurological impairment, which has been and may have been induced by said (neurotropic) infectious agent.

Said (neurotropic) infectious agent can be a microorganism or a prion.

Said use comprises the sequential smelling or sniffing of each composition of said kit, series, or of first, second and third compositions or (functional) association by said subject. The experimenter, laboratory technician or physician records whether said subject succeeds in identifying, within the mixtures or compositions of the same kit, series or (functional) association or use (as an assay performed on a subject), the at least one mixture or composition that contains the (two, or at least two) odorants in a proportion that differs from the other mixture(s) or composition(s).

The person of ordinary skill in the art may appreciate that said sequential smelling or sniffing is advantageously performed under conditions that prevent or avoid olfaction contamination. For example, said sequential smelling or sniffing is advantageously performed in a room where aeration is sufficient to prevent or avoid olfaction contamination, and according to a time sequence, which prevents or avoids olfaction contamination from one mixture or composition to the next mixture or composition.

The person of ordinary skill in the art may appreciate that said sequential smelling or sniffing can be performed under blind testing.

If desired or required, said smelling or sniffing can be repeated with the same and/or with another functional association of the application.

Said use may further comprise detecting failure of said subject to discriminate said first composition from said second composition, or from said second and third compositions.

This failure is an impairment of the olfactory capacity of said subject (compared to a healthy normosmic control subject).

This olfactory discrimination impairment is a biomarker or biological predictor of neurological impairment in said infected subject.

This olfactory discrimination impairment is a biomarker or biological predictor of adverse (long-term) neurological outcome(s) in said infected subject.

Said use may thus further comprise
detecting whether said subject does or not discriminate said first composition from said second composition, or from said second and third compositions, at a first point in time,
detecting whether said subject does or not discriminate said first composition from said second composition, or from said second and third compositions, at a second point in time, wherein said second point in time is different from and posterior to said first point in time,
wherein at least one of said first and second points in time is in a point in time wherein said subject receives or has received a treatment against said (nervous system) infection and/or said neurological impairment, and wherein
detecting an increase in the olfactory discrimination capacity of said subject between said first point in time and said second point in time is indicative that said treatment is therapeutically effective; and/or
detecting a decrease in the olfactory discrimination capacity of said subject between said first point in time and said second point in time is indicative that said treatment is not therapeutically effective.

For example, an increase in the olfactory discrimination capacity is detected when said subject does not discriminate said first composition from said second composition, or from said second and third compositions, at said first point in time, but discriminates said first composition from said second composition, or from said second and third compositions, at said second point in time.

Conversely, a decrease in the olfactory discrimination capacity is detected when said subject discriminates said first composition from said second composition, or from said second and third compositions, at said first point in time, but does not discriminate said first composition from said second composition, or from said second and third compositions, at said second point in time.

The absence of modification of the discrimination capacity of said subject between said first point in time and said second point in time may allow considering that said treatment is not yet therapeutically effective (and that said treatment should be further applied to later determine whether it is or not therapeutically effective).

The application also relates to the use of said kit, series, compositions or (functional) association in the in vivo diagnosis of the severity or extent of said neurological impairment.

The application also relates to the use of said kit, series, compositions or (functional) association in the in vivo diagnosis of response or non-response to a treatment that is intended for treating said neurological impairment and/or said (nervous system) infection. The application also relates to the use of said kit, series, compositions or (functional) association in the treatment of said neurological impairment, wherein said kit, series, compositions or (functional) association is used to monitor or determine whether said treatment improves the olfactory discrimination capacity of said subject. An improvement of said olfactory discrimination capacity is indicative that said treatment is therapeutically effective to treat said neurological impairment and/or said nervous system infection. An absence of improvement of said olfactory discrimination capacity may be indicative that said treatment is not, or not yet, therapeutically effective to treat said neurological impairment and/or said nervous system infection.

Examples of treatment against (nervous system) infection comprise the administration of an antiviral treatment, such as the administration of an acyclic analog of the nucleoside guanosine, for example ganciclovir (9-[(1,3,-dihydroxy-2-propoxy)methyl] guanine, or DHPG) and/or valganciclovir (oral valine ester of ganciclovir). Ganciclovir and/or valganciclovir are typically administered when the infection is a CMV or HCMV infection. Examples of treatment against neurological impairment include the application of a hearing aid (which may e.g., be intended to reduce or limit the progression or extent of the hearing loss).

Said neurological impairment may more particularly be a neurodegeneration, more particularly a (neuro)degeneration of the Central Nervous System (CNS) and/or the Peripheral Nervous System (PNS), more particularly of the CNS, of said (infected) subject. Said neurological impairment may more particularly be a neurological disease or disorder (including a neurodegenerative disease or disorder), more particularly a neurosensory disease or disorder and/or a neurocognitive disease or disorder.

Said neurotropic infectious agent may more particularly be a neurotropic microorganism or prion, more particularly a neurotropic microorganism selected from neurotropic viruses, bacteria, protozoan parasites and fungi, more particularly a neurotropic virus.

Examples of such bacteria include bacteria that may lead to meningitis (such as *Neisseria meningitidis, Streptococcus pneumonia*), bacteria that may lead to *Listeria* Cerebritis or meningoencephalitis (such as *Listeria monocytogenes*), bacteria that may lead to tetanus (such as *Clostridium tetani*), bacteria that may lead to neurosyphylis (such as *Treponema pallidum*), bacteria that may lead to Lyme disease (such as *Borrelia burgdorferi*). Examples of such protozoan parasites include parasites that may lead to toxoplasmosis (such as *Toxoplasma gondii*), parasites that may lead to neuromalaria or cerebral malaria (such as *Plasmodium falciparum*).

Examples of such fungi include fungi that may lead to nervous system infection (such as *Candida glabrata, Aspergillus fumigatus*).

Examples of such viruses include viruses that may lead to rubella (such as rubella virus), viruses of the Herpesviridae family (such as (human) cytomegalovirus or Herpes simplex virus), virus of the *Flavivirus* genus (such as Zika virus), viruses that may lead to viral meningitis (such as Echovirus 30, Coxsackievirus B5).

Examples of such prions include prions that may lead to Creutzfeld-Jakob disease.

Said neurotropic infectious agent may more particularly be a (neurotropic) bacterium selected from *Neisseria, Streptococcus, Listeria, Clostridium, Treponema* and *Borrelia*, more particularly selected from *Neisseria meningitidis, Streptococcus pneumonia, Listeria monocytogenes, Clostridium tetani, Treponema pallidum* and *Borrelia burgdorferi*.

Said neurotropic infectious agent may more particularly be a (neurotropic) protozoan parasite selected from Toxoplasma and Plasmodium, more particularly selected from *Toxoplasma gondii* and *Plasmodium falciparum*.

Said neurotropic infectious agent may more particularly be a (neurotropic) fungus selected from *Candida* and *Aspergillus*, more particularly selected from *Candida glabrata* and *Aspergillus fumigatus*.

Said neurotropic infectious agent may more particularly be a (neurotropic) virus selected from rubella virus, viruses of the Herpesviridae family, viruses of the *Flavivirus* genus, Echoviruses and Coxsackieviruses, more particularly selected from rubella virus, (human) cytomegalovirus, Herpes simplex virus, Zika virus, Echovirus 30 and Coxsackievirus B5.

Said neurotropic infectious agent may more particularly be a (neurotropic) prion.

Said neurotropic infectious agent may more particularly be a (neurotropic) microorganism selected from *Neisseria, Streptococcus, Listeria, Clostridium, Treponema, Borrelia, Toxoplasma, Plasmodium, Candida, Aspergillus*, rubella virus, viruses of the Herpesviridae family, viruses of the *Flavivirus* genus, Echoviruses and Coxsackieviruses. Said neurotropic infectious agent may more particularly be a (neurotropic) microorganism selected from *Neisseria meningitidis, Streptococcus pneumonia, Listeria monocytogenes, Clostridium tetani, Treponema pallidum, Borrelia burgdorferi, Toxoplasma gondii, Plasmodium falciparum, Candida glabrata, Aspergillus fumigatus*, rubella virus, (human) cytomegalovirus, Herpes simplex virus, Zika virus, Echovirus 30 and Coxsackievirus B5.

Said neurotropic infectious agent may more particularly be a (neurotropic) virus, more a (neurotropic) virus selected from viruses of the Herpesviridae family and viruses of the *Flavivirus* genus, more particularly a (neurotropic) virus selected from cytomegalovirus (CMV) and Zika virus (ZIKV), more particularly a (neurotropic) virus from human cytomegalovirus (HCMV) and Zika virus (ZIKV). Said neurotropic infectious agent may more particularly be CMV, more particularly HCMV.

Said neurotropic infectious agent may exhibit tropism for neural stem cells, more particularly for neural stem cells of the human hippocampus and/or of the human olfactory system.

Said neurotropic infectious agent may more particularly be a neurotropic microorganism or prion, more particularly a neurotropic virus, which exhibits tropism for neural stem cells, more particularly for neural stem cells of the human hippocampus and/or of the human olfactory system.

Said neurological impairment is a neurological disability, disease or disorder, or leads (in the absence of therapeutically effective treatment) to a neurological disability, disease or disorder.

Said neurological impairment may more particularly be, or may more particularly lead (in the absence of therapeutically effective treatment), to at least one (i.e., one or several) of
  central or peripheral neuropathies,
  hearing loss, more particularly a hearing loss due to an inner ear damage (more particularly to a damage of the auditory and/or vestibular structures of the inner ear), more particularly SensoriNeural Hearing Loss (SNHL), more particularly nongenetic SNHL,
  mental retardation,
  language retardation or language disability,
  psychomotor retardation or psychomotor disability,
  visual loss, and
  Guillain-Barré syndrome.

Said neurological impairment may more particularly be, or may more particularly lead (in the absence of therapeutically effective treatment), to at least one (i.e., one or several) of
  central or peripheral neuropathies,
  hearing loss, more particularly a hearing loss due to an inner ear damage (more particularly to a damage of the auditory and/or vestibular structures of the inner ear), more particularly SensoriNeural Hearing Loss (SNHL), more particularly nongenetic SNHL,
  mental retardation,
  language retardation or language disability,
  psychomotor retardation or psychomotor disability, and
  visual loss.

This (these) neurological impairment(s) may typically be observed when the subject (or the nervous system of the subject) has been infected by CMV, more particularly by HCMV. Said neurological impairment may more particularly be, or may more particularly lead (in the absence of therapeutically effective treatment), to Guillain-Barré syndrome. Guillain-Barré syndrome may typically be observed when the subject (or the nervous system of the subject) has been infected by ZIKV.

Said subject advantageously is a mammal, more particularly a rodent or a human being, more particularly a human being, more particularly a human being of at least 3-year old. More particularly, said subject is
  a child (of at least 1-year old to less than 12-year old), more particularly a child of 3- to 10-year old,
  a teenager (of at least 12-year old to less than 18-year old),
  an adult (of at least 18-year old to at most 60-year old),
  a pregnant woman, or
  an elderly (of more than 60-year old), more particularly an elderly of more than 65-year old, more particularly an elderly of more than 70-year old, more particularly an elderly of more than 75-year old, more particularly an elderly of more than 80-year old.

More particularly, said subject is
  a child (of at least 1-year old to less than 12-year old), more particularly a child of 3- to 10-year old,
  a teenager (of at least 12-year old to less than 18-year old), or
  a pregnant woman.

Advantageously, said subject is not a fetus or a neonate or an infant (less than 1-year old).

Said subject, who is (or whose nervous system has been) infected by a (neurotropic) infectious agent, may be a subject, who has been congenitally infected.

In other words, said infection (of the nervous system of the subject) may be a congenital infection, i.e., an infection by a microorganism or a prion, more particularly by a virus, which has been (or can be) maternally transmitted to a human fetus, and which has invaded (or can invade) the CNS and/or the PNS, more particularly the CNS, of the human fetus.

Said subject may be the human being (of at least 3-year old), who is born from said fetus.

Said virus can e.g., be CMV, more particularly HCMV.

Said virus can e.g., be CHKV.

Accordingly, the kit, series, compositions or functional association may be used especially for diagnosis of neurological impairment in a subject, in particular in a child, who has been infected by a HCMV, wherein the neurological impairment is identified as an olfactory dysfunction or alteration according to the present invention and wherein said diagnosis is a diagnosis of a risk of development of auditory or neurocognitive deficits. Alternatively, the kit, series, compositions or functional association may be used especially for diagnosis of neurological impairment in a subject, in particular in a child, who has been infected by a ZIKV, wherein the neurological impairment identified as an olfactory dysfunction or alteration according to the present invention and wherein said diagnosis is a diagnosis of a risk of development of neurocognitive deficits.

Said subject, who is (or whose nervous system has been) infected by a (neurotropic) infectious agent, may show symptoms of neurological impairment or neurodegeneration, or may not show any symptom of neurological impairment or neurodegeneration.

Advantageously, the olfactory means of the application allow detecting neurological impairment (or neurodegeneration) at an early stage of the pathological process. The olfactory means of the application thereby allow the application of a treatment against said infection and/or against said neurological impairment or neurodegeneration, at an early stage of the pathological process.

The various embodiments described herein accordingly relate to a kit, series, composition(s) or functional association as disclosed herein for use in in vivo diagnosing a neurological impairment in a subject whose nervous system has been infected by a neurotropic infectious agent, in particular a virus such as CMV, HCMV or ZIKV, in particular a subject affected with congenital infection with such virus, wherein said neurological impairment is detected by means of detection of an alteration of olfactory sensitivity. The neurological impairment may be associated with a risk or with a prognosis for the subject to develop a neurosensory disorder or disease.

In view of the ability of the olfactory means disclosed herein to provide a biomarker for early detection of alteration of olfactory sensitivity in a subject whose nervous system has been infected by a neurotropic infectious agent in particular a virus such as CMV, HCMV or ZIKV, in particular as a result of congenital infection with such viruses, it is also provided herewith a use of the kit, series, compositions or functional association or a method for monitoring said infection, in particular for monitoring its neurological outcomes.

In such a case where infection with CMV, HCMV or ZIKV is known to have taken place, the subject showing alteration of the olfactory sensitivity in a test according to the invention may be oriented for detection of a hearing loss or detection of Guillain-Barré syndrome.

When the infection is a CMV or a HCMV infection, said treatment can e.g., comprise the administration of an acyclic analog of the nucleoside guanosine, such as ganciclovir (9-[(1,3,-dihydroxy-2-propoxy)methyl] guanine, or DHPG) and/or valganciclovir (oral valine ester of ganciclovir).

When the neurological impairment or neurodegeneration is a hearing loss, said treatment can e.g., comprise the application of a hearing aid (which may e.g., be intended to reduce or limit the progression or extent of the hearing loss).

The olfactory means of the application may allow monitoring the development or progression of a neurological pathological process. They may thereby allow detecting an early stage of this process (e.g., a stage that is earlier than the stage at which neurological pathology is established, or a stage that is earlier than the final stage of the neurological pathological process).

The olfactory means of the application may thereby improve the treatment of the subject by making him/her benefiting of the palliative and/or curative effects of the treatment at an earlier or more adequate stage of the pathological process.

The olfactory means of the application can be as described in PCT international application WO 2014/170206 (PCT/EP2014/057277) or in its US counterpart application(s) (e.g., US 2016/0073944 A1). The content of these applications is herein incorporated by reference. More particularly the content of the applications that relate to the olfactory means is herein incorporated by reference.

Said two, or at least two, odorants may be in mixture with a (pharmaceutically-acceptable) vehicle, more particularly a vehicle, which is perceived to be odorless by mammals, or by at least one mammal race or species, advantageously at least by (healthy normosmic) humans (i.e., no odor and no scent perceived by olfactory cognition). Advantageously, said vehicle does not alter the odor or scent emitted by each of said two, or of said at least two, odorants. More particularly, said vehicle is structurally suitable for homogeneously mixing said two, or said at least two odorants, together, such as e.g., a solvent, a cream or a paste. Advantageously, said vehicle is a (liquid) solvent. More particularly, said vehicle is an odorless liquid solvent, such as water, mineral oil or propylene glycol.

Each mixture or composition of the application can be comprised on or in a device or instrument for dispensing odor or scent, more particularly for olfactory testing. More particularly, said first, second and third compositions can each be separately contained in an odor dispensing device for assessing nasal chemosensory performance.

The device or instrument of the application comprises a structure for dispensing the odor(s), scent(s) or smell(s) emitted by the mixture or composition of the application, which is comprised in or on said device or instrument. More particularly, the structure of the device or instrument of the application is adapted, or especially adapted, to sniffing or smelling by a mammal (more particularly by a human), more particularly to active sniffing or smelling by a mammal (more particularly by a human). More particularly, the structure of the device or instrument of the application is adapted, or especially adapted, to allow for a mammal (more particularly for a human) to [actively] sniff or smell the odor(s), scent(s) or smell(s) emitted by said mixture or composition.

More particularly, the olfactory device or instrument of the application is an odor dispensing device for assessing nasal chemosensory performance. It can function as a fully extra-nasal or extra-nostril device or instrument, or as a (partially) intra-nasal or intra-nostril device or instrument.

Devices or instruments for dispensing odor or scent, more particularly for olfactory testing are available to the person of ordinary skill in the art. They include the olfactory devices or instruments that are used in:

the "University of Pennsylvania Smell Identification Test" (UPSIT) [Doty et al. 1984, Physiol. Behav. 32: 489-502; Doty et al. 1984, Laryngoscope 94 (2Pt1): 176-178], commercialized e.g., by Sensonics, Inc. (P.O. Box 112 Haddon Heights, N.J. 08035, USA) as the "Smell Identification TestT", its down-scaled version the "Cross Cultural Smell Identification Test" (CC-SIT) [Doty et al. 1996, Laryngoscope 106 (3Pt1): 353-356], the "Connecticut Chemosensory Clinical Research Center Test" (CCCRC) [Cain et al. 1988, Laryngoscope 98:83-88; Cain 1989, Ear Nose Throat J. 68: 316, 322-328], and the olfactory test battery "SNIFFIN' STICKS™" [Kobal et al. 1996, Rhinology 34: 222-226; Hummel et al. 1997, Chem. Senses 22: 39-52; Kobal et al. 2000, Eur. Arch. Otorhinolaryngol. 257: 205-211; Hummel et al.

2001, Ann. Otol. Rhinol. and Laryngol. 110: 976-981; Hummel et al. 2007, Eur. Arch. Otorhinolaryngol. 364(3): 237-243], commercialized e.g., by Burghardt Messtechnik GmbH (Tinsdaler Weg 175, D-2280 Wedel, Germany; cf. commercial references LA-13-00134, LA-13-00136, LA-13-00138, LA-13-00135 and LA-13-00137; http://www.burhart-mt.de).

The olfactory devices or instruments that are used in tests such as the UPSIT and the CC-SIT test comprise a plurality of cards or booklet pages, which each contain one odorant (or a control substance) embedded therein, e.g., by micro-encapsulation with a binder. The odorant is released by scratching a surface of the card or page.

The olfactory devices or instruments that are used in tests such as the CCCRC test comprise a plurality of bottles or jars, e.g., of polyethylene bottles, which each contain one odorant (or a control substance), e.g., an odorant in liquid form. The bottle or jar is generally provided with a pop-up spout that fits to one or both nostrils and dispenses the odorant to the sniffing user.

The olfactory devices or instruments that are used in tests such as the SNIFFIN' STICKS™ test comprise a plurality of capped felt-tip pens, which each contain one odorant (or a control substance) in a reservoir or absorbent material that is associated with the felt tip of the pen. The pen is de-capped to place the felt tip at a few centimeters from the nostrils (e.g., at about 2 cm), and to smell or sniff the odorant dispensed through the felt tip.

Therefore, examples of an olfactory device or instrument of the application comprise any structure, which can function as a reservoir for odorants and as a dispenser of said odorants, such as:

an absorbent material, more particularly an absorbent fibrous and/or cellulosic material, such as a filter, card or page, optionally provided with microcapsules suitable for entrapping the odorants, a bottle or jar, e.g., a polyethylene bottle, optionally provided with a pop-up spout that fits to one or both nostrils, a pen-like dispensing device, such as a felt-tip pen of said "SNIFFIN' STICKS™" battery.

Advantageously, the structure of the device is adapted to, or especially adapted to, the assessment of nasal chemosensory performance, more particularly the assessment of nasal chemosensory performance of a human.

A kit, series or functional association of the application may therefore comprise at least two or three of said olfactory device or instrument (e.g., at least two or three pen-like dispensing devices, such as felt-tip pens of said "SNIFFIN' STICKS™" battery). A first olfactory device or instrument may contain said first (odorant) composition, a second olfactory device or instrument may contain said second (odorant) composition (and a third olfactory device or instrument may contain said third (odorant) composition).

An odorant is any substance or compound that emits an odor or scent, or any substance or compound that has a distinctive smell. An odor, scent or smell is the odor, scent or smell that is consciously perceived by a mammal by smelling or sniffing though the nostril(s) (olfactory cognition).

Advantageously, an odorant is a substance or compound, which is identifiable (by olfactory cognition) by said mammal, more particularly by the human population to which the odorant is intended, more particularly by a human, more particularly by a healthy normosmic human.

An odorant can be a substance or compound, which is volatile and/or hydrophobic, advantageously volatile and hydrophobic.

Advantageously, an odorant is a substance or compound, which is generally recognized as safe to mammals, more particularly to humans.

Advantageously, an odorant is a compound, more particularly a monomolecular compound.

According to an aspect of the application, each of said at least two odorants, more particularly each of said two odorants, is a monomolecular compound, more particularly a monomolecular compound, which is identifiable by a human by olfaction cognition, still more particularly a monomolecular compound, which is volatile, hydrophobic and identifiable by a (healthy normosmic) human by olfaction cognition, even still more particularly a monomolecular compound, which is volatile, hydrophobic, identifiable by a (healthy normosmic) human by olfaction cognition and generally recognized as safe to humans.

The expression "different odorants" means odorants, which emit different odors or scents. Hence, an odorant is different from another odorant if it emits an odor or scent that is different or perceived to be different from said other odorant. More particularly, an odorant is different from another odorant if the majority of a representative number of normosmic healthy mammals (e.g., healthy normosmic humans) belonging to the same mammal race or species perceives that they emit different odors or scents. For example, an odorant is different from another odorant if more than 40% of a representative number of normosmic healthy mammals belonging to the same mammal race or species perceive that they emit different odors or scents. More particularly, said percentage is more than 45%, more particularly more than 50%, more particularly more than 55%, more particularly more than 60%, more particularly more than 65%. A representative number of normosmic healthy mammals belonging to the same mammal race or species can be determined by the person of ordinary skill in the art depending on the mammal race or species being tested. Such a number generally is more than 10, more particularly more than 20.

According to an aspect of the application, each of said at least two odorants, more particularly each of said two odorants, is a monomolecular compound emitting an odor or scent (as perceived by a healthy normosmic human) selected from the group consisting of anise, apple, banana, caramel, chocolate, cinnamon, clove, cocoa, coconut, coffee, cola, dill, eucalyptus, fish, flower, honey, garlic, ginger, grapefruit, grass, lavender, leather, lemon, lilac, lily of the valley, licorice, melon, mint, mushroom, onion, orange, peach, pear, peppermint, pineapple, rose, spearmint, turpentine, raspberry, sesame oil, smoked meat, soy sauce and vanilla.

According to an aspect of the application, each of said at least two odorants, more particularly each of said two odorants is a monomolecular compound emitting an odor or scent (as perceived by a healthy normosmic human) selected from the group consisting of anise, banana, clove, dill and spearmint.

Examples of monomolecular compounds emitting such an odor or scent comprise:

R-carvone (or L-carvone or carvone −), for spearmint odor or scent,

S-carvone (or D-carvone or carvone +), for dill odor or scent, isoamylacetate or n-butanol, more particularly isoamylacetate, for banana odor or scent, anethol, for anise odor or scent, eugenol, for clove odor or scent,
2-phenylethanol for rose odor or scent,
geraniol for rose odor or scent,
linalool for lily of the valley odor or scent,
cineole for eucalyptus odor or scent,
D-limonene (or R-limonene or limonene +) for orange odor or scent,
L-limonene (or S-limonene or limonene −) for turpentine odor or scent,
menthol for mint odor or scent, and
cinnamon aldehyde for cinnamon odor or scent.

Examples of monomolecular compounds emitting such an odor or scent comprise more particularly:
R-carvone (or L-carvone or carvone −), for spearmint odor or scent,
S-carvone (or D-carvone or carvone +), for dill odor or scent,
isoamylacetate or n-butanol, more particularly isoamylacetate, for banana odor or scent,
anethol, for anise odor or scent, and
eugenol, for clove odor or scent.

Please see e.g., the Arctander atlas (Arctander S. "*Perfume and flavor chemicals*: (*aroma chemicals*)", Allured Publishing Corporation, Carol Stream Ill., 1994).

Please also see the OdorDB database (Yale Center for Medical Informatics, U.S.A.) available on http://senselab.med.yale.edu/odordb/eavObList.aspx?db=5&c1=1.

According to an aspect of the application, each of said at least two odorants, more particularly each of said two odorants is a monomolecular compound selected from the group consisting of R-carvone, S-carvone, isoamylacetate, anethol and eugenol.

As mentioned above, each of said at least two odorants, or each of said two odorants, are different from each other. For example:
one of said at least two, or of said two, odorants is a monomolecular compound emitting spearmint odor or scent (e.g., R-carvone), and the other of said at least two, or of said two, odorants is:
a monomolecular compound emitting dill odor or scent (e.g., S-carvone) or a monomolecular compound emitting banana odor or scent (e.g., isoamylacetate) or
a monomolecular compound emitting anise odor or scent (e.g., anethol) or
a monomolecular compound emitting clove odor or scent (e.g., eugenol), or
one of said at least two, or of said two, odorants is a monomolecular compound emitting dill odor or scent (e.g., S-carvone), and the other of said at least two, or of said two, odorants is
a monomolecular compound emitting spearmint odor or scent (e.g., R-carvone) or
monomolecular compound emitting banana odor or scent (e.g., isoamylacetate) or
a monomolecular compound emitting anise odor or scent (e.g., anethol) or
a monomolecular compound emitting clove odor or scent (e.g., eugenol),
or
one of said at least two, or of said two, odorants is a monomolecular compound emitting banana odor or scent (e.g., isoamylacetate), and the other of said at least two, or of said two, odorants is
a monomolecular compound emitting dill odor or scent (e.g., S-carvone) or
a monomolecular compound emitting spearmint odor or scent (e.g., R-carvone) or
a monomolecular compound emitting anise odor or scent (e.g., anethol) or
a monomolecular compound emitting clove odor or scent (e.g., eugenol),
or
one of said at least two, or of said two, odorants is a monomolecular compound emitting anise odor or scent (e.g., anethol), and the other of said at least two, or of said two, odorants is
a monomolecular compound emitting dill odor or scent (e.g., S-carvone) or
a monomolecular compound emitting banana odor or scent (e.g., isoamylacetate) or
a monomolecular compound emitting spearmint odor or scent (e.g., R-carvone) or
a monomolecular compound emitting clove odor or scent (e.g., eugenol),
or
one of said at least two, or of said two, odorants is a monomolecular compound emitting clove odor or scent (e.g., eugenol), and the other of said at least two, or of said two, odorants is
a monomolecular compound emitting dill odor or scent (e.g., S-carvone) or
a monomolecular compound emitting banana odor or scent (e.g., isoamylacetate) or
a monomolecular compound emitting anise odor or scent (e.g., anethol) or
a monomolecular compound emitting spearmint odor or scent (e.g., R-carvone).

For example, one of said at least two, or of said two, odorants is a monomolecular compound emitting spearmint odor or scent (e.g., R-carvone), and the other of said at least two, or of said two, odorants is a monomolecular compound emitting dill odor or scent (e.g., S-carvone).

For example, one of said at least two, or of said two, odorants is a monomolecular compound emitting banana odor or scent (e.g., isoamylacetate), and the other of said at least two, or of said two, odorants is a monomolecular compound emitting anise odor or scent (e.g., anethol).

For example, one of said at least two, or of said two, odorants is a monomolecular compound emitting anise odor or scent (e.g., anethol), and the other of said at least two, or of said two, odorants is a monomolecular compound emitting clove odor or scent (e.g., eugenol).

In a mixture or composition of the application, said at least two odorants, or said two odorants, are contained in mixture and in any proportion that the person of ordinary skill in the art finds appropriate.

For example, said at least two odorants, or said two odorants, are contained in the mixture or composition of the application in a proportion ranging from 1:1 to 1:5, more particularly in a proportion ranging from 1:1.5 to 1:4, for example in a proportion of 1:1.5, 1:2, 1:2.5, 1:3, 1:3.5 or 1:4. A "X:Y" proportion means X part(s) of one of said at least two, or of said two, odorants for Y part(s) of the other of said at least two, or of said two, odorants (X and Y can identical or different). Said part values are volume parts or weight parts, more particularly volume parts.

For example, said at least two odorants, or said two odorants, are contained in the mixture or composition of the application in a proportion ranging from 0.8%/0.2% to 0.2%/0.8% to 0.2%/0.8%, more particularly in a proportion ranging from 0.6%/0.4% to 0.4%/0.6%, for example in a proportion of 0.8%/0.2%, 0.6%/0.4%, 0.4% 0.6% or 0.2%/

0.8%. A proportion of "X %/Y %" means X % of one of said at least two, or of said two, odorants and Y % of the other of said at least two, or of said two, odorants. A % value of an odorant is the volume or weight, more particularly the volume, of said odorant expressed with respect to the total volume or weight of the mixture in said mixture, more particularly to the total volume of said mixture.

For example, said at least two odorants, or said two odorants, are contained in the mixture or composition of the application in a proportion ranging from 8/2 to 2/8, more particularly in a proportion ranging from 6/4 to 4/6, for example in a proportion of 8/2, 6/4, 4/6 or 2/8. A proportion of "X/Y" means a concentration of X of one of said at least two, or of said two, odorants and a concentration of Y of the other of said at least two, or of said two, odorants. The concentrations X and Y are expressed in the same unit, for example in volume/volume percent, in volume/weight percent or in weight/weight percent, more particularly in volume/volume percent, and are expressed with respect to the total volume or weight of the mixture in said mixture, more particularly to the total volume of said mixture.

For example, one of said at least two, or of said two, odorants is a monomolecular compound emitting spearmint odor or scent (e.g., R-carvone), the other of said at least two, or of said two, odorants is a monomolecular compound emitting dill odor or scent (e.g., S-carvone), and these two odorants are contained in a 2/8 proportion in said first composition and in a 8/2 proportion in said second (or second and third) composition(s).

For example, one of said at least two, or of said two, odorants is a monomolecular compound emitting banana odor or scent (e.g., isoamylacetate), and the other of said at least two, or of said two, odorants is a monomolecular compound emitting anise odor or scent (e.g., anethol), and these two odorants are contained in a 8/2 proportion in said first composition and in a 2/8 proportion in said second (or second and third) composition(s).

For example, one of said at least two, or of said two, odorants is a monomolecular compound emitting anise odor or scent (e.g., anethol), and the other of said at least two, or of said two, odorants is a monomolecular compound emitting clove odor or scent (e.g., eugenol), and these two odorants are contained in a 8/2 proportion in said first composition and in a 2/8 proportion in said second (or second and third) composition(s).

In a kit, series or (functional) association of the application, said several (different) mixtures or compositions are (and remain) distinct or separate from each other. Hence, when they are contained in or on a device or instrument for dispensing odor or scent, they are not mixed together. Advantageously, they are not contained in the same device or instrument. For example, each of said several mixtures or compositions is separately contained in an odor dispensing device for assessing nasal chemosensory performance as above-described (and as below-illustrated).

The odorants are the same in each mixture or composition that belongs to the same kit, series or (functional) association, or use (or assay) i.e., they are the same substances or compounds.

At least one of said several mixtures or compositions contains said odorants in a proportion that differs from the other mixture(s) or composition(s) of the same kit, series or (functional) association or use (assay).

Hence, the proportion of one of said (at least) two odorants with respect to the other of said (at least) two odorants in a first composition of a kit, series or (functional) association or assay is different from their proportion in at least one second composition of the same kit, series or (functional) association or use (assay).

For example, the concentration of at least one odorant in said at least one first mixture or composition is different from its proportion in said at least one second mixture or composition.

For example, the respective concentrations of the (at least two) odorants in said at least one first mixture or composition are different from their respective concentrations in said at least one second mixture or composition.

According to an advantageous aspect of the application, said at least one first composition and said at least one second composition are for sequential use, more particularly for sequential use in the detection of olfactory discrimination impairment in a human, more particularly in a diseased human.

A kit, series or (functional) association or use or assay of the application may comprise any number of mixtures or compositions of the application that the person of ordinary skill in the art may find appropriate. For example, a kit, series, or (functional) association or use or assay of the application may comprise two or three mixtures or compositions of the application.

For example, a kit, series, or (functional) association or use of the application comprises two or three mixtures or compositions of the application, which are distinct or separate from each other, wherein the odorants of said two or three mixtures or compositions are the same but are contained in one of said two or three mixtures or compositions in a proportion that differs from the remaining one or two mixtures or compositions. In the case of a number of three mixtures or compositions of the application, said remaining two mixtures or compositions can be identical, i.e., duplicate.

Advantageously, the difference in proportions within the same kit, series or (functional) association or use is sufficient to be distinguishable by a healthy normosmic human. Hence, according to an advantageous aspect of the application, the at least one mixture or composition, which contains said odorants in a proportion that differs from the other mixture(s) or composition(s) of the same kit, series or (functional) association or use, is consciously perceived (olfactory cognition) as emitting an odor or scent that is different from the odor or scent emitted by the other mixture (s) or composition(s) of the same kit, series or (functional) association or use.

For example, a kit, series or (functional) association or use of the application comprises (at least) two mixtures or compositions of the application, which are distinct or separate from each other, wherein the odorants of each of said (at least) two mixtures or compositions are the same two or the same at least two odorants, and wherein one of said two, or of said at least two, odorants is contained in one of said (at least) two mixtures or compositions in a 8/2 proportion, whereas the other of said two, or of said at least two, odorants is contained in the other of said (at least) two mixtures or compositions in a 2/8 proportion.

For example, a kit, series or (functional) association or use of the application comprises three mixtures or compositions of the application, which are separate from each other (two of said three mixtures compositions being duplicate compositions as described above), wherein the odorants of each of said three mixtures or compositions are the same two or the same at least two odorants, and wherein one of said two, or of said at least two, odorants is contained in one of said three mixtures or compositions in a 8/2 proportion, whereas the other of said two, or of said at least two, odorants is contained in each of the two other (duplicate) mixtures or compositions in a 2/8 proportion.

For example, a kit, series or (functional) association or use of the application comprises (at least) two mixtures or compositions of the application, which are distinct or separate from each other, wherein the odorants of each of said (at least) two mixtures or compositions are the same two or the same at least two odorants, and wherein one of said two, or of said at least two, odorants is contained in one of said (at least) two mixtures or compositions in a 6/4 proportion, whereas the other of said two, or of said at least two, odorants is contained in the other of said (at least) two mixtures or compositions in a 4/6 proportion.

For example, a kit, series or (functional) association or use of the application comprises three mixtures or compositions of the application, which are separate from each other (two of said three mixtures compositions being duplicate compositions as described above), wherein the odorants of each of said three mixtures or compositions are the same two or the same at least two odorants, and wherein one of said two, or of said at least two, odorants is contained in one of said three mixtures or compositions in a 6/4 proportion, whereas the other of said two, or of said at least two, odorants is contained in each of the two other (duplicate) mixtures or compositions in a 4/6 proportion.

For example, a kit, series or (functional) association or use of the application comprises (at least) two mixtures or compositions of the application, which are distinct or separate from each other, wherein the odorants of each of said (at least) two mixtures or compositions are R-carvone and S-carvone in mixture, and wherein one of said (at least) two mixtures or compositions contains R-carvone and S-carvone in a 8/2 proportion, whereas the other of said (at least) two mixtures or compositions contains R-carvone and S-carvone in a 2/8 proportion.

For example, a kit, series or (functional) association or use of the application comprises three mixtures or compositions of the application, which are separate from each other (two of said three mixtures compositions being duplicate compositions as described above), wherein the odorants of each of said three mixtures or compositions are R-carvone and S– carvone in mixture, and wherein one of said three mixtures or compositions contains R-carvone and S-carvone in a 8/2 proportion, whereas each of the two other (duplicate) mixtures or compositions contains R-carvone and S-carvone in a 2/8 proportion.

For example, a kit, series or (functional) association or use of the application comprises (at least) two mixtures or compositions of the application, which are distinct or separate from each other, wherein the odorants of each of said (at least) two mixtures or compositions are isoamylacetate and anethol in mixture, and wherein one of said (at least) two mixtures or compositions contains isoamylacetate and anethol in a 8/2 proportion, whereas the other of said (at least) two mixtures or compositions contains isoamylacetate and anethol in a 2/8 proportion.

For example, a kit, series or (functional) association or use of the application comprises three mixtures or compositions of the application, which are separate from each other (two of said three mixtures compositions being duplicate compositions as described above), wherein the odorants of each of said three mixtures or compositions are isoamylacetate and anethol in mixture, and wherein one of said three mixtures or compositions contains isoamylacetate and anethol in a 8/2 proportion, whereas each of the two other (duplicate) mixtures or compositions contains isoamylacetate and anethol in a 2/8 proportion.

For example, a kit, series, or (functional) association or use of the application comprises (at least) two mixtures or compositions of the application, which are distinct or separate from each other, wherein the odorants of each of said (at least) two mixtures or compositions are anethol and eugenol in mixture, and wherein one of said two (at least) mixtures or compositions contains anethol and eugenol in a 8/2 proportion, whereas the other of said (at least) two mixtures or compositions contains anethol and eugenol in a 2/8 proportion.

For example, a kit, series or (functional) association or use of the application comprises three mixtures or compositions of the application, which are distinct or separate from each other (two of said three mixtures compositions being duplicate compositions as described above), wherein the odorants of each of said three mixtures or compositions are anethol and eugenol in mixture, and wherein one of said three mixtures or compositions contains anethol and eugenol in a 8/2 proportion, whereas each of the two other (duplicate) mixtures or compositions contains anethol and eugenol in a 2/8 proportion.

A mixture or composition of the application, more specifically a kit, series or (functional) association or use of the application, or a collection of kits, series or (functional) associations of the application, can be further functionally associated with, or can further comprise, any other additional element, such as at least one additional means, device, instrument, composition, substance or compound, that the person of ordinary skill in the art finds appropriate to measure olfactory capacity, more particularly to detect and/or measure olfactory impairment.

For example, said additional element can be means for measuring the olfactory detection threshold of a mammal or human, more particularly a diseased mammal or human.

Means for measuring olfactory detection threshold can for example comprise a plurality of compositions, wherein each composition of said plurality contains only one odorant, and wherein all the compositions of said plurality contains the same one odorant and form a serial dilution of said same one odorant.

Said odorant can be as defined above. For example, said odorant can be n-butanol or 2-phenylethanol. Please see Hummel et al. 1997, Chem. Senses 22: 39-52.

The term "comprising", which is synonymous with "including" or "containing", is open-ended, and does not exclude additional, un-recited element(s), ingredient(s) or method step(s), whereas the term "consisting of" is a closed term, which excludes any additional element, step, or ingredient which is not explicitly recited.

The term "essentially consisting of" is a partially open term, which does not exclude additional, un-recited element(s), step(s), or ingredient(s), as long as these additional element(s), step(s) or ingredient(s) do not materially affect the basic and novel properties of the invention.

The term "comprising" (or "comprise(s)") hence includes the term "consisting of" ("consist(s) of"), as well as the term "essentially consisting of" ("essentially consist(s) of"). Accordingly, the term "comprising" (or "comprise(s)") is, in the application, meant as more particularly encompassing the term "consisting of" ("consist(s) of"), and the term "essentially consisting of" ("essentially consist(s) of").

In an attempt to help the reader of the application, the description has been separated in various paragraphs or sections. These separations should not be considered as disconnecting the substance of a paragraph or section from the substance of another paragraph or section. To the contrary, the description encompasses all the combinations of the various sections, paragraphs and sentences that can be contemplated.

Each of the relevant disclosures of all references cited herein is specifically incorporated by reference. The following examples are offered by way of illustration, and not by way of limitation.

EXAMPLES

Neurodegeneration is also a common feature of infection by many neurotropic viruses and bacteria, such as congenital cytomegalovirus (CMV) and Zika virus (ZIKV). Congenital CMV and ZIKV are major public health concern due to severe sequelae in the fetus and newborn and the absence of treatment. In developed countries, 1% of newborns are CMV-infected and at risk of developing neurocognitive and sensorineural handicaps. During the epidemic of ZIKV in French Polynesia, the frequency of microcephaly in fetuses and neonates from ZIKV-infected mothers was about 1%. Moreover, severe neurological complications such as Guillain-Barré syndrome were found following ZIKV infection in adults (Watrin et al., 2016).

To date, the mechanisms, biomarkers and biological predictors of adverse neurological outcomes to these viral infections remain poorly known. We believe that no study has hitherto examined the impact of congenital CMV or ZIKV infection on olfaction. Our hypothesis is that a link may exist between neuroinvasion, neurodegeneration and olfactory impairment, and that olfactory impairment may be a clinical marker for possible neurological outcome in these infections.

Example 1

Murine Model of Congenital CytoMegaloVirus (CMV) Infection

Cytomegalovirus (CMV) causes severe materno fetal infections, leading to sensorineural handicaps including profound hearing loss that can emerge several years after the congenital infection (Williamson W. D., et al., 1992). In the human fetus, CMV infection leads to irreversible olfactory bulb (OB) damage (Tessier N., et al.; 2014). Here, we demonstrate that congenital murine CMV strikes the OB and leads to major olfactory deficits in mice. While sensory inputs to the OB remain unchanged, CMV reduces the size of OB glomeruli, depletes dopaminergic cells in the OB and decreases cell proliferation in the neurogenic subventricular zone (SVZ). Olfactometry experiments reveal an alteration of olfactory perception and lack of fine olfactory discrimination, in particular of binary mixtures of monomolecular odorants. Despite differences in brain neurogenesis between human and mouse (Lui J. H., et al., 2014), together these findings offer new strategies aiming at early detection of CMV-associated neurological dysfunctions caused by congenital infections.

The high sero-prevalence of Herpes virus type 5 or CMV amongst the population constitutes a major public health concern due to the possible severe sequelae in the fetus and newborn, and the absence of vaccine or curative treatment so far (Fowler K. B., et al. 2006; Manicklal S., et al. 2013). CMV is transmitted through bodily fluids and infection is usually asymptomatic or can have a flu-type presentation, except when transmitted from mother to fetus. CMV belongs to the TORCH class of most common agents affecting the fetal/neonatal brain and transmitted in utero or intrapartum, including Toxoplasmosis, *Listeria*, Rubella, Herpes simplex and recently Zika virus (Coyne C. B., et al. 2016). In developed countries, CMV infection is to date the first cause of congenital malformations. In utero infection can strike peripheral and central nervous system with hematopoietic and neural stem cell damage (Tsutsui, Y., 2009; Teissier, N., et al, 2011; Sakao-Suzuki, M., et al. 2014). In developed countries, 50-85% of adults are infected before the age of 40 (Cannon, M. J., et al., 2010). One percent of newborns are CMV-infected and at high risk of developing learning disabilities and hearing loss thus requiring prolonged follow-up (Williamson, W. D. et al., 1992; Townsend, C. L., et al., 2013).

To date, very few prognosis tools of neurosensory sequelae have been developed; they include ultrasound examination of macroscopic brain abnormalities and viral burden at birth (Forner, G. et al., 2015). CMV exhibits particular tropism for hematopoietic precursors (Ibanez, C. E., et al. 1991; Cloarec R., et al. 2016) and neural stem cells of the olfactory system of fetuses (Teissier, N. et al., (2014); van Den Pol, et al., 1999; Odeberg J. et al., 2006), thus lesioning the OB, but no study has hitherto examined the impact of the virus on olfaction. Other studies have reported olfactory deficit caused by neurotoxic and viral lesions (Lazarini, F., et al., 2014; Khodosevich, K. et al., 2013). Olfactory disorders precede neurological disorders and olfaction is the best correlate of Parkinson's disease (Godoy, M. D., et al. 2015; Nalls, M. A. et al., 2015). In the latter, hyposmia may in part reflect neurodegeneration within the OB as there is evidence that OB degeneration precede both nigral degeneration and symptoms (Braak, H. et al. 2002). For this reason, early detection of olfactory impairment might represent a valuable prognosis tool for congenital CMV infection.

We investigated olfaction in an animal model of congenital CMV infection. This model was achieved via in utero intraplacental inoculation of murine CMV in pregnant Oncins France 1 (OF1) mice under deep anesthesia (FIG. 1a) (Tsutsui Y, 2009; Sakao-Suzuki et al., 2014). It was confirmed that this model evoked a hearing loss phenotype and brain alterations that are reminiscent of what is observed in infants with congenital CMV infection. Recordings of auditory brainstem responses (ABR) show that hearing thresholds increase by about 20 dB in adult infected mice (FIG. 1e, consistent with refs (Woolf, N. K., et al., 1989; Juanjuan, C. et al., 2011; Schachtele, S. J. 2011).

Similarly, CMV-infected mice exhibit impaired hidden food search (FIG. 2a), but not when food was made visible (FIG. 2b). Three olfactory dimensions could be compromised by CMV: odorant detection, discrimination and/or learning. To specify if they were equally sensitive to CMV infection, congenitally-infected mice were tested using automated olfactometers (FIG. 2c-e).

We accordingly assessed odorant perception, discrimination and memory, using operant discrimination paradigms in automated olfactometers. We found an alteration of olfactory perception in CMV-infected mice. Moreover, we found that congenital CMV infection leads to disruption in the discrimination of odorants, more particularly of binary mixtures of monomolecular odorants.

These data allowed us to propose an olfactory test for early detection and treatment of neurological diseases based on the assessment of discrimination of binary odorant mixtures. This test is non-invasive, easy to use even in children and fast (about 15 minutes).

Design of the Experiments—Material and Methods

Pups of OF1 pregnant mice from Charles Rivers were intraplacentally inoculated under anesthesia (isoflurane)

with murine CMV (Smith strain, ATCC-VR1399) at 10(4.75)TCID 50/0.2 ml or PBS at embryonic day 13 as described by Sakao-Suzuki et al. 2014. Hearing loss was assessed using auditory evoked potentials.

Then the olfactory performance of 13 of these mice (11 CMV-infected male mice and 2 sham mice that received PBS) as well as of 9 control male animals (of the same age as the CMV-infected mice) were assessed by custom-made olfactometers, as previously described (Siopi et al., 2016). The timetable of the experiments is shown in FIG. 1 (E: embryonic; W: week). The results of the 2 sham mice have been pooled with the results of the 9 control mice.

Data Analysis and Statistics

Data were analyzed using GraphPad Prism (GraphPad Software, USA). Results are expressed mean±s.e.m. The statistical test and sample size (n) for each experiment are specified in the figure legend. The complete statistical analysis for each experiment (evaluated parameter, comparison, exact P values, degree of freedom) is given in Tables A and B. Normally distributed data were analyzed by two-tailed unpaired Student t test and two-way regular or repeated measures analysis of variance (ANOVA) as appropriate. Non-normally distributed data were analyzed by Gehan-Breslow-Wilcoxon or Mann-Whitney tests as appropriate. No statistical method was used to predetermine sample size, but it is consistent with previous publications.

Auditory Brainstem Responses (ABR)

Hearing loss was assessed using ABR (OtoPhylab, RT Conception, France) (Nguyen, U. et al. 2009; Scimemi, P. et al., 2014). Needle electrodes were placed subcutaneously under anesthesia with ketamine (40 mg/kg) and xylazine (4 mg/kg). The reference electrodes were inserted beneath the pinna of the ears, the ground beneath the skin of the neck and the active electrode beneath the skin of the back. Headphones with appropriate earplugs were used as acoustic transducers. Clicks were delivered in range 12-30 Hz. Filter settings were at 150-3000 Hz. Responses from 1000 sweeps were averaged at each intensity level. Initially, the click intensity was reduced by 20 or 10 dB steps sound pressure level (SPL) then by 5 dB SPL steps near threshold. A contralateral auditory masking was used for high intensity stimulations (>45 dB).

The threshold was defined as the lowest intensity at which a clear IV waveform was visible in the evoked trace and was determined by visual inspection of the responses in blind of the mouse group.

Recording and Analysis of Ultrasonic Vocalizations.

The recording of ultrasonic calls began 30s after placing the pup in the custom-made chamber isolator of the olfactometer (www.olfacto-meter.com) as described in ref Lemasson et al. (2005). Ultrasonic vocalizations were detected using an ultrasonic microphone connected to a bat detector (frequency range 10-130 kHz, Magenta BATS digital bat detector, RSPB, UK) that converts ultrasonic sounds to the audible frequency range. Using the broadband 60 kHz output of the detector, ultrasonic calls were sampled, recorded and analyzed using Audacity open software (www.audacityteam.org). Ultrasonic emissions were recorded during the 5-min-isolation time of the pup into the olfactometer during three successive test periods: the first period without any odorant (1 min), the second period with exposure to social or non social odorant (1 mn) and the last period with exhaust odorant (1 min and 30 s). The social odorant is a male scent from 10 g of soiled bedding from a group of 6 unfamiliar male adult OF1 mice. The non-social odorant is an odorant scent delivered from 10 ml of liquid 10% mineral oil dilution of citral (Sigma). After testing, pups were immediately put back with their mother. The mean rate of ultrasonic emissions (call/min) was computed for each time block.

Olfactory Testing

Odorants. All odorants were monomolecular compounds from SIGMA-ALDRICH (SIGMA-ALDRICH CHEMIE S.A.R.L.; L'Isle d'Abeau Chesnes; 38297 Saint-Quentin Fallavier; France), dissolved in water or mineral oil as indicated below.

n-butanol has a rancid scent or odor.

D-limonene has orange scent or odor; citronellal has citronella scent or odor; anethol has aneth (or anise) scent or odor; and IsoAmylAcetate (IAA) has banana scent or odor.

Burried Food Finding Test

To assess olfaction, we used the buried food finding test after 20 h of food deprivation as described (Lazarini F. et al., 2012). About 10 pieces of "Coco Pops" cereals were hidden in the corner of the test cage under bedding. The mouse was placed in the opposite corner and the latency to find the food within a 15 min period was recorded food (defined as the time to locate cereals and start digging). Thirteen minutes later, mice performed the same test but with visible coco pops, positioned upon the bedding.

Automated olfactometers. Mice were partially water-deprived by receiving 1-2 ml/day of water for one week and then trained on a "go-no go" discrimination task in computer-controlled four-channel olfactometers with custom-made mouse chamber isolator (cf. FIG. 2). As described in Siopi et al. (2016), mice were trained to respond to the presence of an odorant (positive stimulus, S+) by licking the water delivery tube situated out of the odorant sampling port (5 cm distance). They were also trained not to respond on the presentation of another odorant or solvent (negative stimulus, S−). A single stimulus (S+ or S−) was randomly presented at each trial. Each series of 20 trials comprises 10 presentations of the rewarded odorant and 10 presentations of the non-rewarded odorant. Licking response following an S+ trial and no licking following an S− trial are scored as correct, and called hit and correct rejection respectively. About 10 µl of water were delivered as a reward in a hit. A licking response following an S− trial and no licking following an S+ trial were scored as error and named false alarm and miss respectively. Accuracy (percentage of correct responses) was scored for each series of 20 trials [(hits+correct rejections)/20×100]. Olfactory performances were assessed using monomolecular odorant compounds and binary odorant mixtures. Mice were given a session of 8 to 10 series of 20 trials per day. All odorants were diluted in water or mineral oil just before the experiments, and their concentrations are given as the dilution of the odorant in the saturator bottles.

Odorant detection threshold. Mice were trained in olfactometers to recognize n-butanol as the rewarded stimulus (S+). Mice have to detect successively descending decimal concentrations of n-butanol (S+) diluted in water. In each session, water served as the S−. Mice were given one to two sessions per day with one decimal dilution of the odorant per session. The session ended at the criterion performance achievement (75% of correct response in the series of 20 trials). If the criterion performance was not achieved in two successive sessions with the same odorant dilution, the preceding dilution was considered as the detection threshold.

Odorant discrimination tasks. Mice were trained to discriminate between:

D-limonene (dilution 10$^{-2}$ in mineral oil, S+) and Citronellal (dilution 10$^{-2}$ in mineral oil S−) (simple discrimination task);

D-limonene (dilution 10$^{-2}$ in mineral oil, S+) and Anethol (dilution 10$^{-2}$ in mineral oil S−) (simple discrimination task);

0.1% IsoAmylAcetate (IAA, dilution 10$^{-3}$ in water, S+) and Anethol (S−) diluted in mineral oil (simple discrimination task).

Then, olfactory discrimination performance was assessed for two IAA-Anethol mixture tasks (difficult discrimination task) as follows:

in the first task, S+ was a solution of 0.8% IAA and 0.2% Anethol, and S− was a solution of 0.2% IAA+ and 0.8% Anethol;

in the second task, S+ was a solution of 0.6% IAA and 0.4% Anethol, and S− was a solution of 0.4% IAA and 0.6% Anethol.

Long-Term Memory Test.

Mice were given 4 daily training sessions of 8 blocks of 20 trials for D-limonene Anethol discrimination task (S+ was a solution of D-limonene at dilution 10-2 in mineral oil, and S− was a solution of Anethol dilution 10-2 in mineral oil). Mice were then left for 30 days in their home cages, subjected to partial water deprivation for the 7 last days. No water was given on day 29; the following day, each mouse was subjected to a 20-trial memory test for the 2-odorant tasks. No reinforcement (reward) was given for correct responses in this session.

Bromodeoxyuridine Injections.

Mice were intraperitoneally injected with a DNA synthesis marker, 5 Bromo-2'-deoxyuridine (BrdU; 100 mg/kg, Sigma-Aldrich). They received four injections, at 2 h intervals, on a single day, 4 weeks before perfusion, for the analysis of cell survival.

Stereotaxic Lentiviral Injection.

The SVZ neurogenesis continuously produces new neurons for the OB (Lledo P. et al., 2006). These new neurons migrate along the RMS toward the OB. To label them, we injected 200 nl of a replication-deficient lentivector expressing GFP into the RMS as described (Nissant A., et al., 2009).

Immunohistochemistry, Confocal Imaging and Quantification.

Mice were anesthetized with sodium pentobarbital (i.p., 100 mg/kg, Sanofi, France) and perfused transcardially with a solution containing 0.9% NaCl and heparin (5×103 U/ml, Sanofi) followed by 4% paraformaldehyde in phosphate buffer. Forty-micrometer coronal brain sections were obtained using a vibrating microtome (VT1000S, Leica). Immunostaining was performed on free-floating sections as described (Siopi E. et al., 2016) using anti-OMP (1:2000; Wako), anti-TH (1:4000; Immunostar), anti CB (Swant; 1:2000), anti-CR (Swant; 1:2000), anti-BrdU (1:1000; Abcys), anti-Ki67 (1:500; Abcam), anti NeuN (5 µg/ml; Millipore), anti-murine CMV (specific of IE1 protein; 1:1000, kindly given by S. Jonjic) (Cekinovic D. et al., 2008), anti-IBA1 (1:400; Wako) and anti-CD68 (1:2000; Serotec).

For cell counting, 4-8 slices separated by 120 µm were selected for each animal. Whole-OB or SVZ mosaics were obtained using an Olympus BX51 microscope (20× objective) and the Compix Imaging software (Hamamatsu Photonics) for the analysis of immunoperoxidase-labeled cells, or the spinning disk confocal microscope Cell Voyager (CV1000, Yokogawa) for the analysis of immunofluorescent) labeled cells. The borders of the SVZ, RMS, GL, GCL and glomeruli were delineated blinded to the results. Positive cells were automatically counted using the "spot detector" tool of the Icy open source platform (www.icy.bioimage.analysis.org) (de Chaumont, F. et al., 2012).

Results and Discussion

1. Olfactory Detection

We investigated olfactory sensitivity by determining the detection threshold for n-butanol odorant, using the descending method of limits in a two-odorant rewarded discrimination task. Mice were given two sessions per day with one decimal dilution of the odorant per session. CMV-infected mice needed more trials to learn to distinguish between n-butanol and its water solvent (FIG. 2d). CMV infection resulted in an increase of the detection threshold of around three orders of magnitude (FIG. 2e, left). While all control mice were able to detect diluted n-butanol, two CMV-infected mice out of 8 were unable to achieve the performance criterion even for pure n-butanol (FIG. 2e, right).

As shown in FIG. 2e, congenital CMV infection impairs olfactory acuity. It induces a significant decrease in the detection threshold of around three orders of magnitude (3.0±1.5 vs 6.0±1.9, t(15)=3.238; p<0.01 vs CTL). While all CTL (control) mice were able to detect strong dilutions of n-butanol, two CMV-infected mice upon 8 were unable to achieve the performance criterion even for pure n-butanol (FIG. 2e).

2. Olfactory Discrimination

Given the strong effects of CMV on olfactory perception, we investigated the possible effects on olfactory discrimination. The same paradigm was used for simple olfactory discrimination tasks between two odorants and for difficult olfactory discrimination tasks between binary mixtures of odorants (FIG. 3), using strong concentrations. We found that CMV-infected mice have altered discrimination of odorants, and in particular when binary mixtures of monomolecular odorants were used (i.e., difficult task).

Congenital CMV infection alters the ability of mice to discriminate between IAA and Anethol in the simple olfactory discrimination task (FIG. 3a). The acquisition rate was significantly lower for CMV-infected mice compared to CTL (two-way ANOVA with repeated measures, virus factor: F(1, 17)=5,837; p<0.05). As shown in FIGS. 3c and 3g, CMV-infected mice needed more trials to learn to discriminate between these two odorants (t(15)=2,674 p<0.05). Similarly, CMV-infected mice required more trials to learn to distinguish between n-butanol and water (FIGS. 2d and 2g, t(14)=3,213 p<0.01), D-Limonene and citronellal (FIGS. 3d and 3h), D-limonene and anethol (FIGS. 3e and 3h, t(17)=2,398 p<0.05).

In the difficult discrimination task of binary IAA-Anethol mixtures (FIG. 3a), the 6/4 vs 4/6 mixtures of IAA-Anethol could not be correctly discriminated by the CTL mice (FIG. 3b, right panel), and the CMV-infected mice could neither achieve correct discrimination (FIG. 3b, right panel). The 8/2 vs 2/8 more contrasted mixtures of IAA-Anethol could be correctly discriminated by the CTL mice (FIG. 3b, left panel), and the performance of CMV-infected animals was significantly poorer compared to CTL (two-way ANOVA with repeated measures, virus factor: F (1, 17)=14.63, p<0.01 for the 8/2 vs 2/8 mixture; FIG. 3b, left panel).

Discrimination of binary (i.e., bi-odorant) mixtures (FIG. 3b, left panel) provides much higher detection sensitivity (p<0.01) than the mono-odorant test (FIG. 2d).

Altogether these data indicate that CMV-infected mice have a decreased olfactory acuity and a reduced olfactory discrimination, particularly in binary mixtures of odorants. Analysis of long-term olfactory memory indicates no difference between CMV-infected and CTL mice (FIG. 30. Altogether these data indicate that CMV-inoculated mice exhibit poorer odorant detection and olfactory discrimination while olfactory memory remains intact.

Figure 4:
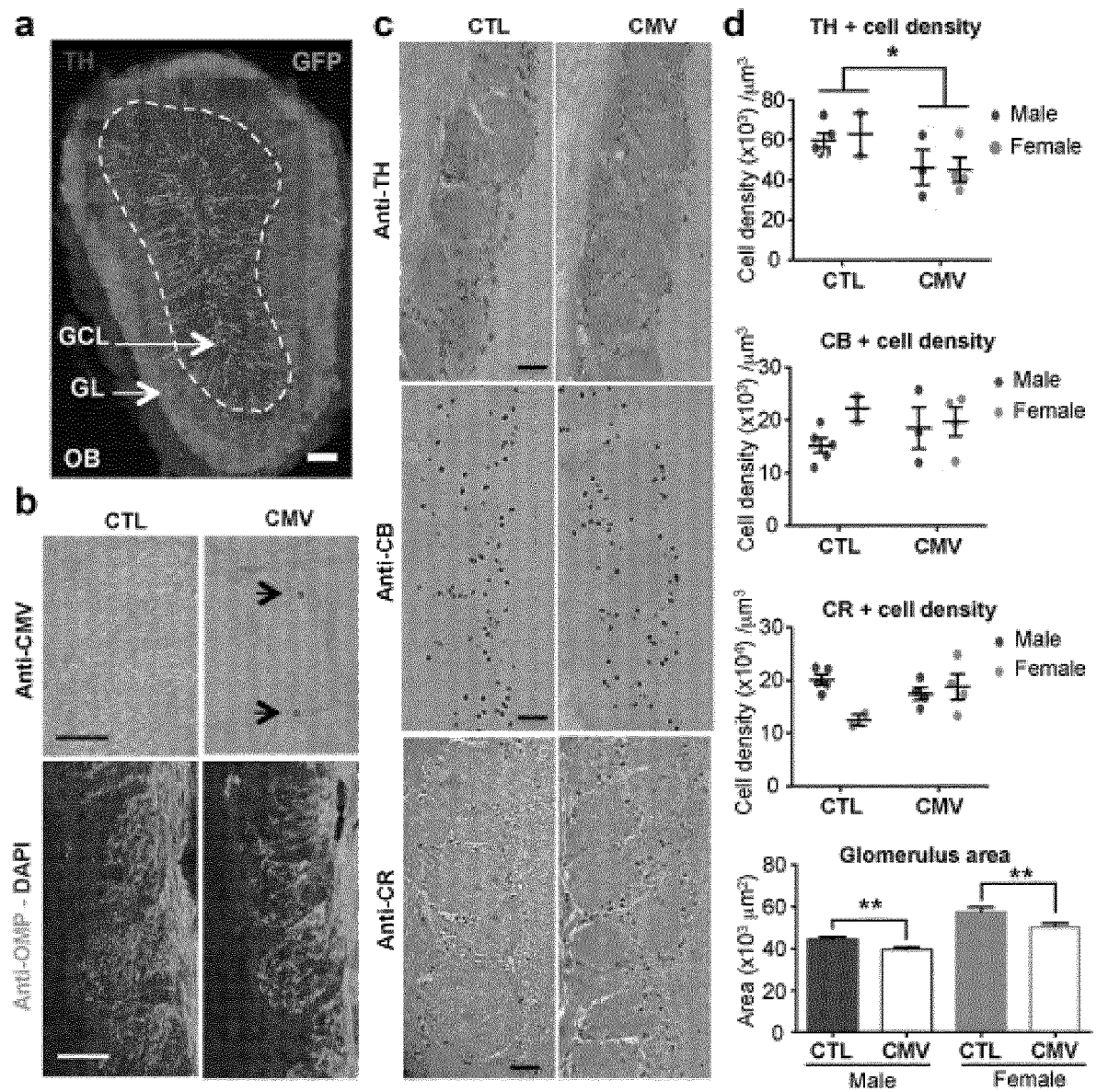
FIG. 4. Impact of CMV congenital infection on the OB. a, Coronal section of a murine OB showing the GCL and the GL. Dopaminergic neurons (tyrosine hydroxylase+, TH) are red stained and neo-neurons are green labeled by a GFP expressing viral vector (see Methods). b, c, Representative staining of coronal OB slices with murine CMV IE1 (b), Olfactory Marker Protein (OMP) expressed by OSN (b), TH (c), CB (c) and CR (c) specific antibodies, showing OSN, TH+, CB+, CR+ and CMV+ cells in CTL and congenital CMV-infected mice. d, TH+, CB+ and CR+ cell densities in the GL and glomerulus (glom) size at 4 months after birth following congenital CMV inoculation. For cell density analysis, n=5 male CTL, n=2 female CTL, n=4 male CMV, n=4 female CMV. For glom size, n=212 glom from 2 CTL females, n=409 glom from 4 CMV females, n=499 glom from 4 CTL males, n=262 glom from 4 CMV males. Results in d are mean±s.e.m. P values are calculated by ANOVA. Scales bars: 100 μm in a, 50 μm in b, c.
Figure 6:
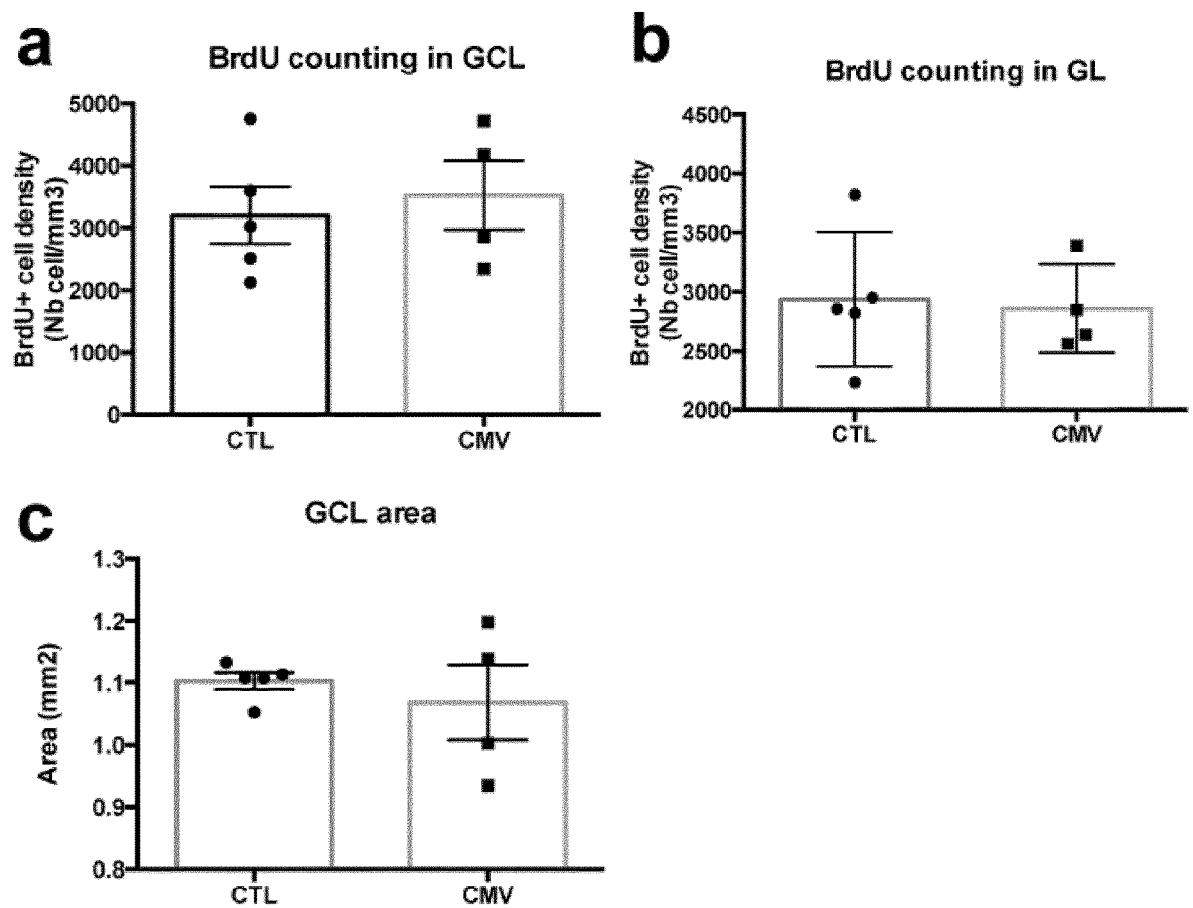
FIG. 6. Adult neurogenesis in the OB and the DG. BrdU+ cell density in the GCL (a) and the GL (b); Size of the GCL (c) at 4 months after birth following congenital CMV inoculation. Results are expressed mean±s.e.m. n=5 male CTL, n=4 male CMV. P value is calculated by Student t test (a, b) and Mann-Whitney test (c).

Because the OB circuit constitutes the first central relay station of the olfactory system, bridging the nose with higher brain structures, the olfactory deficits we report here may result either from CMV lesioning the olfactory sensory inputs, from direct damage to the OB circuit, and/or the olfactory cortex. Olfactory sensory neurons (OSN) of the nasal epithelium project via the olfactory nerve to the superficial glomerular layer (GL) of the OB. OSN synapse on the dendrites of output mitral/tufted cells on organized structures called glomeruli (Lledo, P. M., et al. 2006). Immunohistochemical analysis of the brains 4 months after birth shows viral expression in the GL of CMV-infected mice (FIG. 4a,b) consistent with a previous study (Cekinovic D., et al. 2008). Despite the presence of viral particles, OSN innervation to the OB of CMV-infected mice is similar to CTLs (FIG. 4b). This finding is reminiscent to previous observation that peripheral infection with some neurotropic viruses, such as Bunyaviruses, leads to specific brain neuroinvasion via OB capillaries but not through OSN axons (Winkler, C. W. et al., 2015). Further anatomical investigations demonstrate that the viral OB neuroinvasion was accompanied by a reduced mean size of glomeruli in infected animals (FIG. 4d). Conversely, congenital CMV infection does not change the size of the granule cell layer (GCL) of the OB (FIG. 6c), which is composed of GABAergic interneurons that regulate the neuronal activity of output OB neurons.

Changes in glomeruli's size prompted us to check whether a specific neuronal population was missing. We found that CMV-infected mice show a reduced population of dopaminergic cells in the OB glomeruli (FIG. 4a,c,d). The cell density of two other glomerular populations, Calbindin (CB)- and Calretinin (CR)-positive cells are similar to the CTL mice, indicating higher vulnerability for bulbar dopaminergic neurons to CMV infection (FIG. 4c,d). The depletion in dopaminergic cells observed in CMV-infected animals might reflect the damage of dopaminergic neurogenesis, direct viral damage or neuroinflammation-induced cell death. Dopaminergic neurons play a key role in olfactory detection of social and non-social odorants and their damage lead to dramatic olfactory deficit (Lazarini, F., et al., 2014). As the peak of the dopaminergic cell recruitment in the rodent OB occurs during early postnatal life (De Marchis, S. et al., 2007), at the maximum of the brain growth (Semple. B. D., et al., 2013), it is probable that bulbar dopaminergic neurons are impacted during this time window by congenital CMV infection.

Figure 5:
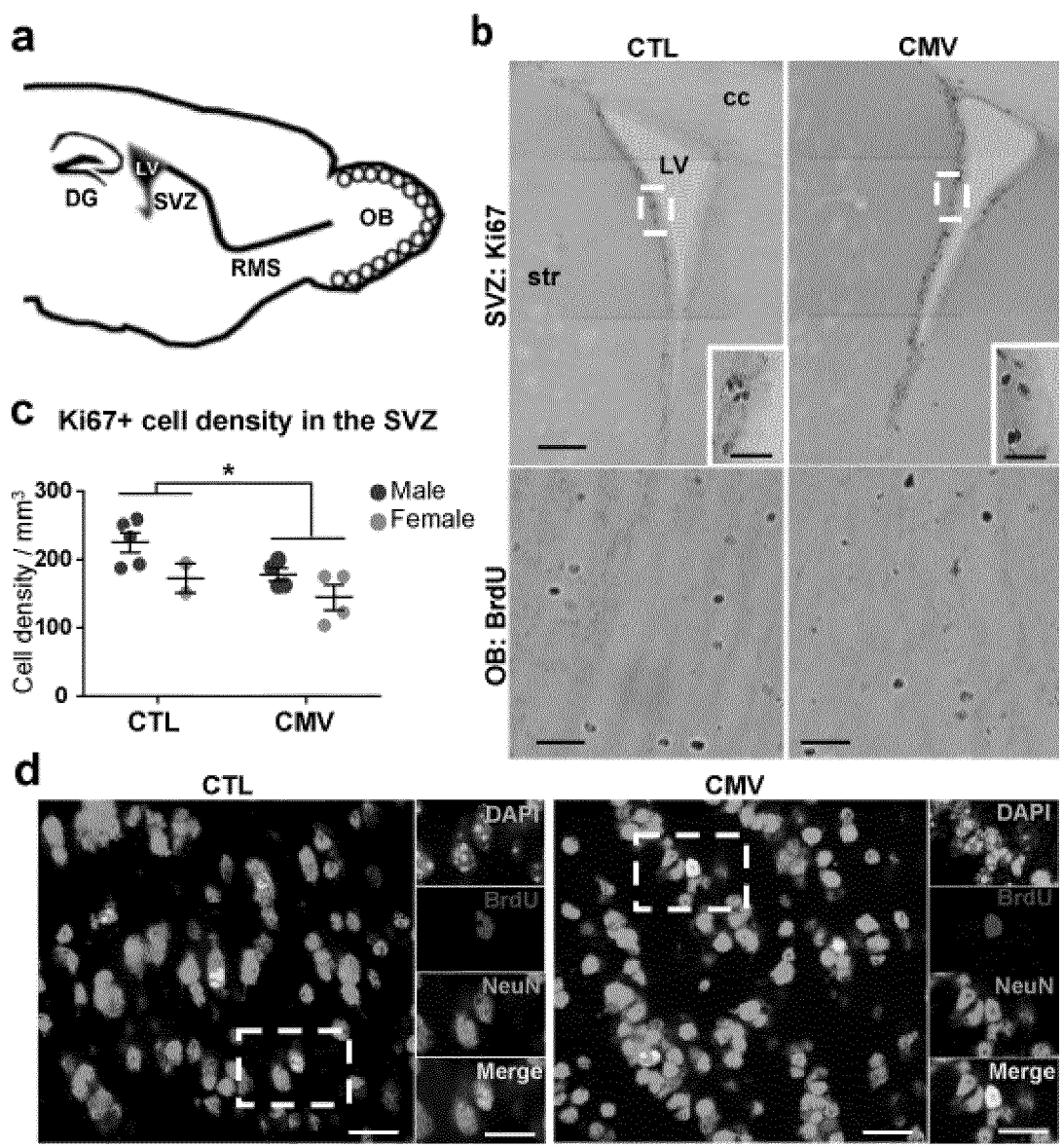
FIG. 5. CMV congenital infection impairs precursor cell proliferation in the SVZ. a. Sagittal section of a murine brain showing the neurogenic dendate gyrus (DG) of the hippocampus, the lateral ventricle (LV), the neurogenic SVZ, the rostral migratory stream (RMS) and the OB. Neuroblasts born in the adult SVZ migrate via the RMS until the OB where they differentiate into GCL or GL interneurons. b, d. Representative staining of coronal SVZ and OB slices with Ki67 (b), BrdU (b,d), 4',6-diamidino-2-phenylindole (DAPI) (d) and neuronal marker NeuN (d) antibodies, showing Ki67+ neural progenitor cells and BrdU+ adult-born neurons in CTL and congenital CMV-infected mice at 4 months after birth following congenital CMV inoculation. Results are expressed mean±s.e.m. n=5 male CTL, n=4 male CMV. P value is calculated by ANOVA. Scale bars: 100 μm in b, up, 50 μm in b, down, 5 μm in d.

It is important to note that the neurogenic SVZ provides the adult OB with dopaminergic cells all life long. In rodents, the SVZ gives rise to thousands of neuroblasts per day that migrate toward the OB where they functionally integrate pre-existing neuronal circuits and differentiate mostly in granule cells and glomerular interneurons (Lledo, P. M. et al., 2006). We found a decreased cell proliferation in the SVZ (FIG. 5a-c) supporting the view that CMV affects adult neurogenesis in mice. We analyzed the survival rate of newly-generated neurons in the OB, by counting BrdU+ cells one month after BrdU injection. No difference was found between the number of BrdU+ cells counted in infected and CTL animals (FIG. 6a,b), suggesting that CMV impaired the cell proliferation of newly-generated OB neurons at adult stage, but not their survival in the OB (Sui, Y. Horne et al., 2012). Thus, CMV-infected mice exhibit OB structural abnormalities, compromised neurogenesis and fewer bulbar dopaminergic cells that might support their olfactory deficit. Further experiments are required to clarify the time course of both neuro-invasion and neurogenesis attack, and to elucidate the viral mechanisms of neuronal loss in this model.

TABLE A

Complete statistical analysis of behavioural experiments

| Behavioral paradigm | Measurement | Statistical test | Comparison | Statistics | df | P | FIG. |
|---|---|---|---|---|---|---|---|
| Auditory brainstem responses | Threshold | Unpaired t-test | CMV vs CTL | t = 4.715 | 14 | 0.0003*** | 1e |
| Buried food finding | Buried food: Latency | Gehan-Breslow-Wilcoxon test | CMV vs CTL | $Chi^2$ = 4.032 | 1 | 0.0446* | 2a |
|  | Visible food: Latency | Gehan-Breslow-Wilcoxon test | CMV vs CTL | $Chi^2$ = 0.0067 | 1 | 0.9348 ns | 2b |
| Olfactometry | Discrimination (n-butanol vs water) | Gehan-Breslow-Wilcoxon test | CMV vs CTL | $Chi^2$ = 8.945 | 1 | 0.0028** | 2d |
|  | Threshold | Unpaired t-test | CMV vs CTL | t = 3.238 | 15 | 0.0055** | 2e |
|  | Discrimination (isoamylacetate vs anethol) | Two-way repeated measures ANOVA | Factor 1 virus | F = 5.837 | 1 | 0.0272* | 3a |
|  |  |  | Factor 2 block | F = 6.948 | 39 | <0.0001**** |  |
|  |  |  | Interaction F1 × F2 | F = 0.7764 | 39 | ns |  |
|  | Mixture discrimination (8/2 vs 2/8) | Two-way repeated measures ANOVA | Factor 1 virus | F = 14.63 | 1 | 0.0014** | 3b |
|  |  |  | Factor 2 block | F = 7.232 | 7 | <0.0001**** |  |
|  |  |  | Interaction F1 × F2 | F = 7.061 | 7 | <0.0001**** |  |
|  | Mixture discrimination (6/4 vs 4/6) | Two-way repeated measures ANOVA | Factor 1 virus | F = 0.3243 | 1 | 0.5765 ns | 3b |
|  |  |  | Factor 2 block | F = 1.975 | 7 | 0.064 ns |  |

TABLE A-continued

Complete statistical analysis of behavioural experiments

| Behavioral paradigm | Measurement | Statistical test | Comparison | Statistics | df | P | FIG. |
|---|---|---|---|---|---|---|---|
| | | | Interaction F1 × F2 | F = 0.4241 | 7 | 0.8856 ns | |
| | Discrimination (isoamylacetate vs anethol) | Gehan-Breslow-Wilcoxon test | CMV vs CTL | $Chi^2$ = 4.560 | 1 | 0.0327* | 3c |
| | Discrimination (D-limonene vs Citronellal) | Gehan-Breslow-Wilcoxon test | CMV vs CTL | $Chi^2$ = 7.425 | 1 | 0.0064** | 3d |
| | Discrimination (D-limonene vs Anethol) | Gehan-Breslow-Wilcoxon test | CMV vs CTL | $Chi^2$ = 4.735 | 1 | 0.0296* | 3e |
| | Olfactory memory (D-limonene vs Anethol) | Two-way repeated measures ANOVA | Factor 1 virus | F = 1.821 | 1 | 0.1949 ns | 3f |
| | | | Factor 2 block | F = 25.20 | 1 | 0.0001*** | |
| | | | Interaction F1 × F2 | F = 3.728 | 1 | 0.0704 ns | | df, degree of freedom;
ns, non significant.

TABLE B

| Evaluated Parameter | Location | Statistical test | Comparison | Statistics | df | p | FIG. |
|---|---|---|---|---|---|---|---|
| TH + cell density | Olfactory bulb (GL) | Two-way ANOVA | Factor 1 virus | F = 5.374 | 1 | 0.0429* | 4d |
| | | | Factor 2 gender | F = 0.02459 | 1 | 0.8785 ns | |
| | | | Interaction F1 × F2 | F = 0.9973 | 1 | 0.6356 ns | |
| CB + cell density | Olfactory bulb (GL) | Two-way ANOVA | Factor 1 virus | F = 2.223 | 1 | 0.1668 ns | 4d |
| | | | Factor 2 gender | F = 0.02489 | 1 | 0.8785 ns | |
| | | | Interaction F1 × F2 | F = 0.9973 | 1 | 0.6356 ns | |
| CR + cell density | Olfactory bulb (GL) | Two-way ANOVA | Factor 1 virus | F = 3.332 | 1 | 0.0952 ns | 4d |
| | | | Factor 2 gender | F = 1.042 | 1 | 0.3292 ns | |
| | | | Interaction F1 × F2 | F = 6.591 | 1 | 0.0262* | |
| Glomerulus area (males) | Olfactory bulb (GL) | Unpaired t-test | CMV vs CTL | t = 2.681 | 680 | 0.0075** | 4d |
| Glomerulus area (females) | Olfactory bulb (GL) | Unpaired t-test | CMV vs CTL | t = 2.647 | 619 | 0.0083** | 4d |
| Ki67 + cell density | SVZ | Two-way ANOVA | Factor 1 virus | F = 5.374 | 1 | 0.0467* | S1c |
| | | | Factor 2 gender | F = 0.02459 | 1 | 0.0271* | |
| | | | Interaction F1 × F2 | F = 0.9973 | 1 | 0.5977 ns | |
| BrdU + cell density | Olfactory bulb (GCL) | Unpaired t-test | CMV vs CTL | t = 0.4509 | 7 | 0.6657 ns | S2a |
| BrdU + cell density | Olfactory bulb (GL) | Unpaired t-test | CMV vs CTL | t = 0.2297 | 7 | 0.8249 ns | S2b |
| GCL area | Olfactory bulb (GCL) | Mann-Whitney test | CMV vs CTL | U = 10 | 7 | >0.999 ns | S2c |

Figure 7:
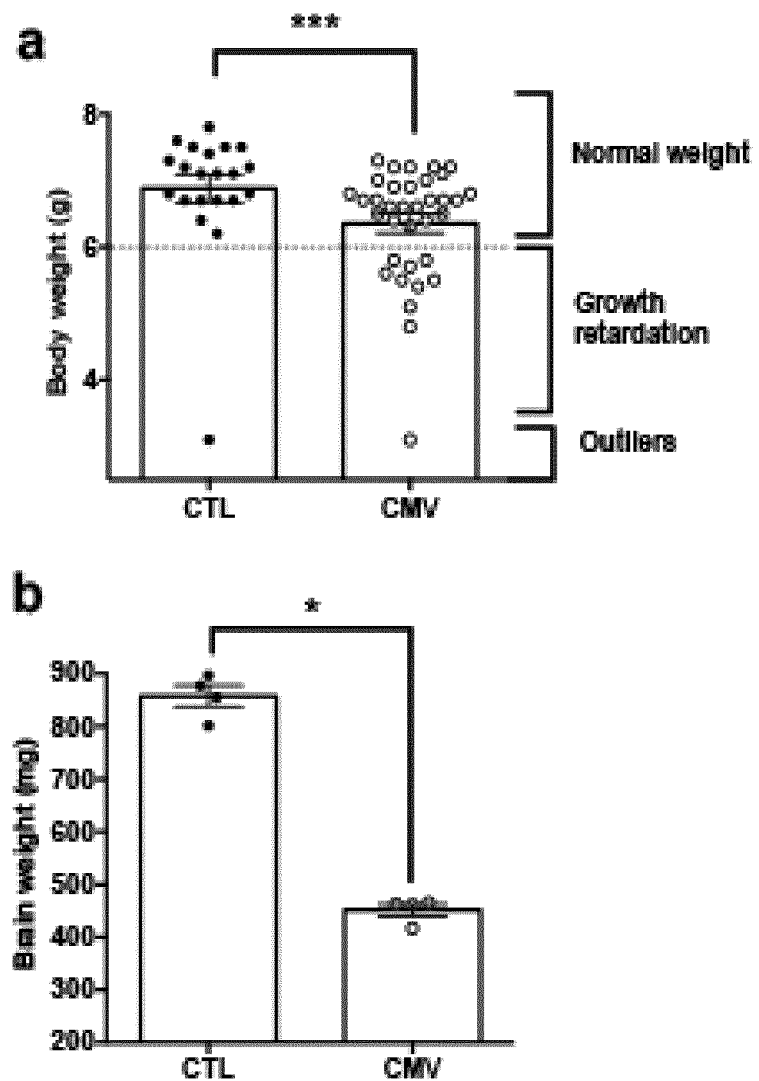
FIG. 7. Impact of CMV congenital infection on growth. a, Body weight of the post-natal 8-day-old mice after infection with murine CMV at day 13 of gestation (n=21 CTL, n=35 CMV). CTL mice were injected with saline only. Outliers were identified by ROUT. Variances between the CTL and CMV groups without outliers are different ($F(33,19)=2.433$, $P<0.05$), underlying the growth retardation of 9/34 CMV pups. b, Brain weight of the post-natal 21-day-old mice after infection with murine CMV at day 13 of gestation. CTL mice were injected with saline only. n=4 male mice per group. P values are calculated by Mann-Whitney test. *$P<0.05$; ***$P<0.001$; mean±s.e.m. in bar graphs.

We accordingly confirmed that placental infection with murine CMV (FIG. 1 a&b) induces developmental retardation and microcephaly reminiscent to congenital CMV infection in humans (8 day-old pups, CTL body weight: 7.065±0.1 g; CMV body weight: 6.44±0.11 g Mann-Whitney U (53)=15; p<0.001 vs CTL, FIG. 7a; 21 day-old male pups, CTL brain weight: 857.5±20.44 mg, CMV brain weight: 451.5±11.5 mg Mann-Whitney U (7)=0; p<0.05 vs CTL, FIG. 7b).

Growth retardation was observed in 25% of offsprings exposed to infection in utero (9 pups upon 34, consistent with Li & Tsutsui, 2000). Moreover, we confirmed that this model develops a hearing loss phenotype reminiscent to what has been reported in infants with congenital CMV infection. Recordings of auditory brainstem responses (ABR) show no difference in hearing thresholds between control and infected mice at week 4 after birth but an increase by about 20 dB in adult infected mice (86.25±2.455 vs 65.00±3,780 dB; t(14)=4.532; p<0.001 vs CTL, FIG. 1$e$).

Figure 8:
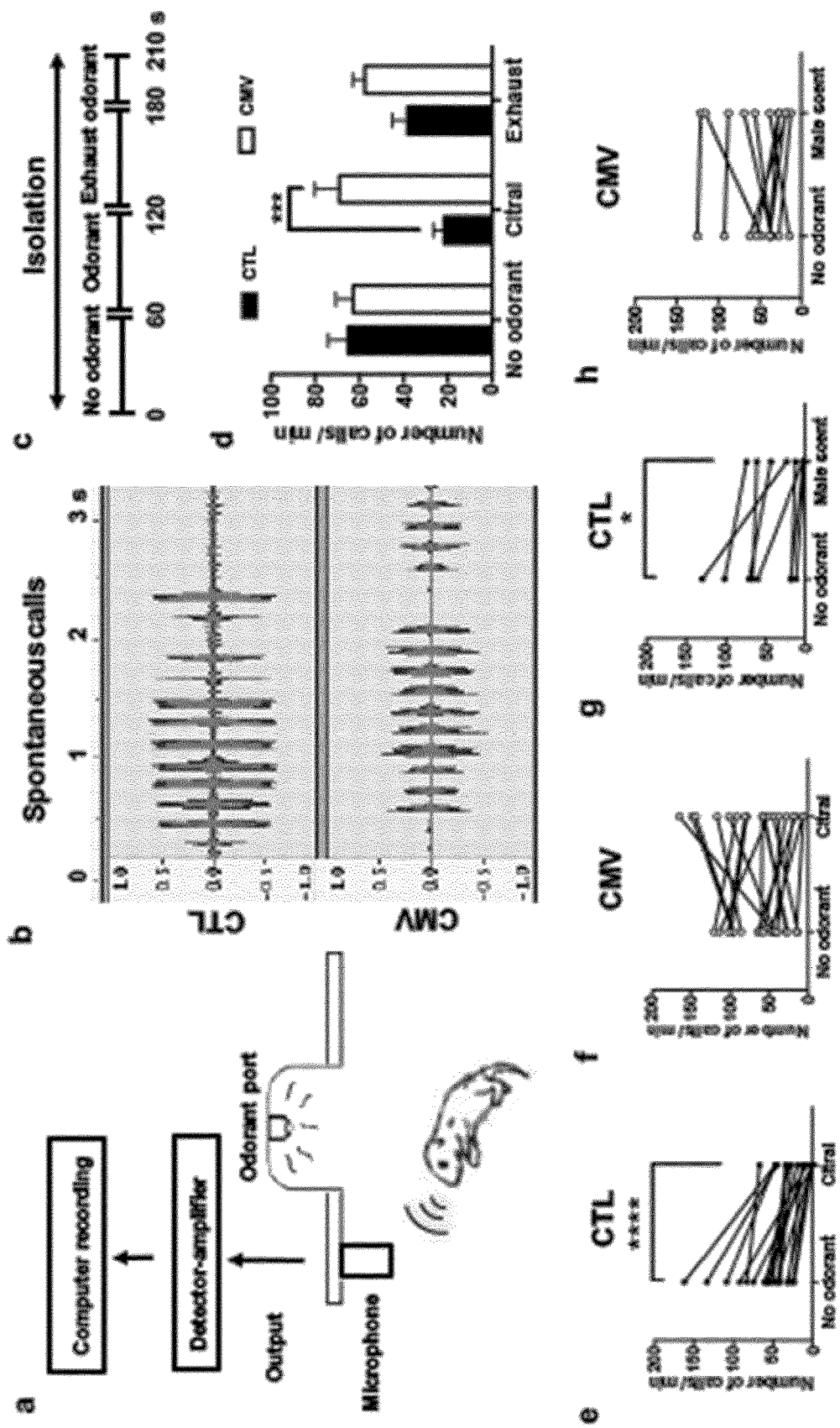
FIG. 8. Impact of CMV congenital infection on neonate olfaction. a, Emission and quantitation of ultrasonic vocalizations. The recording of ultrasonic calls began 30 s after placing the pups in the test chamber of the olfactometer. Ultrasonic vocalizations were detected using an ultrasonic microphone connected to a bat detector that converts ultrasonic sounds to the audible frequency range. b, Typical wave traces of spontaneous call series from pre-weaning 6-day-old pups after congenital CMV infection. CTL was inoculated with saline only. c, Timetable of the experiments. Mice were infected in utero with CMV or received saline at E13. They were analyzed using olfactometers as early as 6 days after birth. Their ultrasonic emissions responses were recorded during the first period without odorant (1 min), followed by the period of odorant exposure (1 min) and finally the last period of exhaust odorant (1 Min and 30 s). d, e, f, Ultrasonic calls for citral odorant on day 6 after birth (n=18 CTL, n=19 CMV). d, g, h, Ultrasonic calls for male scent odorant on day 8 after birth (n=18 CTL. n=8, n=11 CMV). P value are calculated by two-way ANOVA with repeated measures followed by Sidak multiple comparison test (d) or two-sided paired Student's t-test (e, f, g, h). *$P<0.05$, *$P<0.001$, **$P<0.0001$; mean±s.e.m. in bar graphs.

We found that pups with placental MCMV infection exhibit impaired olfactory perception as early as 6 days post birth (FIG. 8). After separation from their mother and isolation in an olfactometer chamber, pre-weaning pups produce ultrasonic calls that promote mother-offspring interaction (FIG. 8$b$, consistent with Branchi et al., 1998, Lemasson et al. 2005). CMV-infected pups also emit such ultra-vocalizations following isolation (FIG. 8$b$). As expected, CTL pups decrease their emission of calls in response to exposure to non-social or social odorant molecules such as citral (21.67±4.83 vs 65.22±9.011 calls/min; t(17)=6.07 p<0.0001 vs no odorant, FIG. 8$e$) or male scent (47)=2.617 p<0.05 vs no odorant, FIG. 8$g$). In contrast, congenital CMV infection impairs the ultrasonic call responses triggered by these odorants (FIGS. 8$d$ & $h$), indicating an alteration of olfactory perception induced by the virus as early as post-natal day 6 (citral: CMV vs CTL, 69.05±11.14 vs 21.67±4.83 calls/min, t(105)=4.244; p<0.001, FIG. 8$d$).

Figure 2:
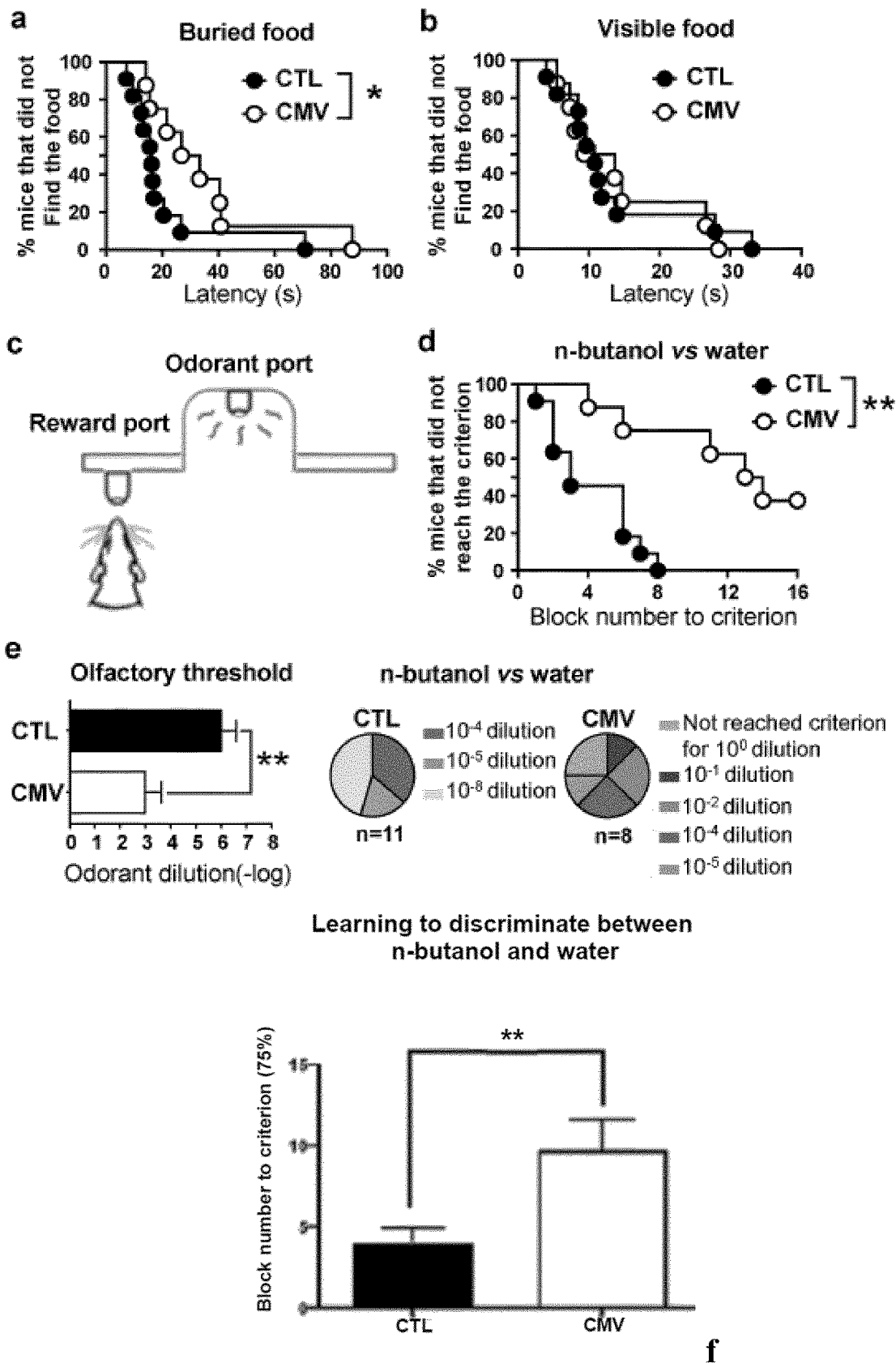
FIG. 2: Impact of CMV congenital infection on olfaction. a, b, Latency to find the buried (a) or visible (b) food reward in the buried food-finding test. Results are % of mice that did not find the food over a 15 min period. P value is calculated by Gehan-Breslow-Wilcolxon test. (a) c, Go-no go procedure. The olfactometer isolator comprises an odorant sampling port and a water delivery tube to reward mice. Animals are trained to distinguish between 2 odorants: a positive stimulus (S+) and a negative stimulus (S−). The olfactometer isolator is ventilated for fast odorant removal. A licking response following an S+ trial and no licking following an S− trial were scored as correct. d, % of mice that did not reach the criterion performance (75% correct responses in the block) on a discrimination task using n-butanol ($10^{-3}$ dilution) and its solvent (water). e, f, Effects of congenital CMV infection on olfactory detection. Results are expressed as detection thresholds ($-\log_{10}$ of odorant dilution; mean±s.e.m.) for n-butanol (left) or the % of mice for the last dilution performance criterion (right). A block is a series of 20 trials with random 10 S+ and 10 S−. n=8 CMV, n=11 CTL. P values are calculated by Gehan-Breslow-Wilcoxon test (a, b, d) and two-sided Student's t test (e). *$P<0.05$, **$P<0.01$.

Similarly, CMV-infected adult mice exhibit impaired hidden food search ($Chi^2$=4.032, p<0.05; FIG. 2$a$), but not when food was made visible (FIG. 2$b$), thus confirming olfactory deficits induced by virus exposure in utero.

Three olfactory dimensions could be compromised by CMV: odorant detection, discrimination and/or learning. To specify if they were equally sensitive to CMV infection, congenitally-infected adult mice were tested using automated olfactometers.

The present study showed that direct infection of the placenta with CMV may efficiently cause growth retardation and that it has marked deleterious effects on hearing and olfaction. Here we provide direct evidence that olfactory behavioral deficits are present in 6 postnatal-day offsprings after placental infection with MCMV (FIG. 8) while no difference in hearing was observed in offsprings on postnatal day 28 (FIG. 1$e$). Altogether, these data suggest that CMV-induced olfactory dysfunction may represent an early phenotype with prognostic value for the future development of auditory or neurocognitive deficits.

Conclusion and Perspectives

The murine model of congenital CMV infection showed that the olfactory perception threshold is altered by CMV infection. Moreover, we revealed that CMV-infected mice perform poorly in the task that involves fine discrimination of binary mixtures of monomolecular odorants, and that olfactory testing with such binary mixtures is much more sensitive than mono-odorant olfactory testing.

Therefore, olfactory testing with binary mixtures of monomolecular odorants is an indicator of neurological impairment. It is useful for the early diagnosis and treatment of neurodegenerative diseases and neurological complications after bacterial or viral infection. For instance, in congenital CMV infection, hearing loss may occur several years after birth in childhood and be often progressive. Exploration of olfaction in congenital CMV infection might allow early detection of starting deterioration of hearing or predict the occurrence of deafness by assessing the presence of CMV in the central nervous system and thus probably in the inner ear. Identification of children that are susceptible to hearing impairment is of major interest because it will condition increased surveillance of these children and early treatment by use of a hearing aid minimizing the impact of this deficit on the cognitive development. Also, early detection of olfactory deficit might be relevant to anticipate a reduced food intake and loss of social olfactory cues important to maintain a strong parent-infant bound. Our preclinical findings provide experimental support for clinical trials in congenital CMV infection. Assessing olfaction could lead to novel strategies to monitor this infection including long-term neurological outcome.

Example 2

Clinical Research Study on Children with Congenital CMV Infection

The results shown in example 1 above allowed us to propose an olfactory test for neurological outcomes in humans, including children, based on the assessment of discrimination of binary odorant mixtures (3 different binary mixtures: carvone (+), carvone (−) mixture (8/2 and 2/8 proportions), isoamylacetate/anethol (8/2 and 2/8 proportions) and anethol/eugenol (8/2 and 2/8 proportions).

Odorants (all from SIGMA-ALDRICH) are considered safe and are used in food and cosmetic products. Odorants are presented in SNIFFIN' STICKS™ (see Hummel et al. 1997) commercialized by BURGHARDT MESSTECHNIK GmbH (Tinsdaler Weg 175, D-2280 Wedel, Germany). For the discrimination of mixtures, 3 sticks are presented to the subject, two containing the same odorant mixture and one a different associated odorant mixture. The subject is requested to indicate the stick that smells different. This test is non-invasive, easy to use even in very young children and fast (15 minutes).

The performance of this test is assessed in a clinical research study on children of 3- to 10-year old (after oral consent of the child and written informed consent of the two parents), i.e.:

80 children with congenital CMV infection (40 children with symptomatic CMV infection at birth and 40 children with asymptomatic form of CMV infection at birth) and 40 healthy controls (matched for age and gender), led by the Pediatric ENT Department of Robert Debré Hospital, Paris, France (see the clinical protocol INFECSMELL CLIN CoRC N° 2015-091).

The children shall not have any chronic sinusitis nor any nasopharyngitis.

CMV infection is diagnosed by positive CMV PCR in urine and/or blood in the first 3 weeks of life. Retrospective diagnosis can be made based on the presence of a positive PCR on the Guthrie test performed at 3-7 days of life.

CMV infection is considered symptomatic at birth typically when at least one of the following clinical signs is present at birth: growth retardation, prematurity, petechiae, splenomegaly, thrombocytopenia, jaundice, low number of platelets, ictere, digestive disorders.

Each children sequentially smells or sniffs three SNIFFIN' STICKS™ (a red stick, a green stick and a blue stick), each containing a mixture of carvone (+) and carvone (−) [problem n° 1]. These three sticks all contain the same two odorants but one of them differs by the proportion of these two odorants [proportion of 2/8 in two sticks, proportion of 8/2 in the third stick]. The same test is conducted with a mixture of isoamylacetate (IAA) and anethol [problem n° 2], and a mixture of anethol and eugenol [problem n° 3].

carvone (+)=D-carvone=S-carvone carvone (−)=L-carvone=R-carvone

TABLE 1

| | Color of the SNIFFIN' STICKS ™ | | |
|---|---|---|---|
| | red | green | blue |
| Problem no1 | Mix of L-carvone and D-carvone in a 8/2 proportion | Mix of L-carvone and D-carvone in a 2/8 proportion | Mix of L-carvone and D-carvone in a 8/2 proportion |
| Problem no2 | Mix of IAA and anethol in a 2/8 proportion | Mix of IAA and anethol in a 8/2 proportion | Mix of IAA and anethol in a 2/8 proportion |
| Problem no3 | Mix of anethol and eugenol in a 2/8 proportion | Mix of anethol and eugenol in a 2/8 proportion | Mix of anethol and eugenol in a 8/2 proportion |

The correct answers are the green stick for problem n° 1, the green stick for problem n° 2 and the blue stick for problem n° 3.

A score of 1 is given to a child who correctly identifies the sticks that differs from the two other sticks. An incorrect answer results in a score of zero. Olfaction is considered normal if a child gets a total score of 2 or 3 after having answered the three problems [problems n° 1, n° 2 and n° 3]. Olfaction is considered altered if the total score is 0 or 1.

The total score reflects the olfactory discrimination capacity of the child, and is compared to the CMV status, more particularly to the symptomatic CMV or asymptomatic CMV status.

The nature and extent of any neurological impairment are determined for each child. In congenitally CMV infected children, auditory thresholds are assessed by either subjective audiograms or objective evoked potentials. In control patients, the normality of hearing is screened using Evoked OtoAcoustic Emissions (EOAEs).

The score of each child at the olfactory discrimination capacity is compared to the nature and extent of the neurological impairment, more particularly to the extent of the hearing deficiency, in the CMV-infected children compared to the healthy children.

The olfactory capacity of each child is also measured using SNIFFIN' STICKS™ that do not contain a mixture of odorants, but that contain only one odorant, e.g., a series of three sniffing sticks, wherein two of the sticks contain anethol, whereas the third one contains IAA.

A translational clinical research study is currently ongoing on children with congenital CMV infection and their matched controls (see https://clinicaltrials.gov/ct2/show/study/NCT02782988).

Example 3

Clinical Research Study on Patients with Zika Virus (ZIKV) Infection

The tests described in example 2 above are assayed in a ZIKA-cohort of French Caribbean population. This clinical research may be accessed at:

ZIKASMELL clinical trial: Contribution of detecting olfactory disorders in the early detection of neurological disorders related to Zika virus infection during the 2016-17 epidemic in the Antilles-Guyane. Ancillary study of Cohort of Patients infected by an arbovirus (CARBO). N° CorC 2016-050 (approval on Dec. 16, 2016), N° CPP 2010-55 (approval on Sep. 12, 2016), NCT02782988 (https://clinicaltrials.gov/ct2/show/NCT01099852). Sponsor: CHU-Martinique (CHU-M). Support: PHRC & REACTing. Ancillary study Director: F Lazarini, Clinical investigators: A Lannuzel (PI, CHU Guadeloupe), A Cabié (CHU-M), F Djosou (CH Guyane), S Matheron (CHU Bichat, Paris).

398 adults and children from 3-10 years, with acute Zika infection. Study end: 2019

BIBLIOGRAPHIC REFERENCES

Williamson, W. D., Demmler, G. J., Percy, A. K. & Catlin, F. I. *Progressive hearing loss in infants with asymptomatic congenital cytomegalovirus infection. Pediatrics* 90, 862-866 (1992)

Teissier, N., et al. *Cytomegalovirus-induced brain malformations in fetuses. J. Neuropathol. Exp. Neurol.* 7, 143-158 (2014).

Lui, J. H., et al. *Radial glia require PDGFD-PDGFRβ signalling in human but not mouse neocortex. Nature* 515, 264-268 (2014).

Fowler, K. B. & Boppana, S. B. *Congenital cytomegalovirus (CMV) infection and hearing deficit. J. Clin. Virol.* 35, 226-231 (2006).

Manicklal, S., Emery, V. C., Lazzarotto, T., Boppana, S. B. & Gupta, R. K. The "silent" global burden of congenital cytomegalovirus. *Clin. Microbiol. Rev.* 26, 86-102 (2013).

Coyne, C. B. & Lazear, H. M. Zika virus—reigniting the TORCH. *Nat Rev Microbiol.* 14, 707-715 (2016).

Tsutsui, Y. *Effects of cytomegalovirus infection on embryogenesis and brain development. Congenit Anom (Kyoto)* 49, 47-55 (2009).

Teissier, N., et al. Inner ear lesions in congenital cytomegalovirus infection of human fetuses. *Acta neuropathologica* 122, 763-774 (2011).

Sakao-Suzuki, M., et al. *Aberrant fetal macrophage/microglial reactions to cytomegalovirus infection. Ann. Clin. Trans'. Neurol.* 1, 570-588 (2014).

Cannon, M. J., Schmid, D. S. & Hyde, T. B. *Review of cytomegalovirus seroprevalence and demographic characteristics associated with infection. Rev. Med. Virol.* 20, 202-213 (2010).

Townsend, C. L., et al. Long-term outcomes of congenital cytomegalovirus infection in Sweden and the United Kingdom. *Clin. Infect. Dis.* 56, 1232-1239 (2013).

Forner, G., Abate, D., Mengoli, C., Palù, G. & Gussetti, N. *High Cytomegalovirus (CMV) DNAemia Predicts CMV Sequelae in Asymptomatic Congenitally Infected Newborns Born to Women With Primary Infection During Pregnancy. J. Infect. Dis.* 212, 67-71 (2015).

Ibanez, C. E., Schrier, R., Ghazal, P., Wiley, C. & Nelson, J. A. *Human cytomegalovirus productively infects primary differentiated macrophages. J. Virol.* 65, 6581-6588 (1991).

Cloarec, R., et al. *Cytomegalovirus Infection of the Rat Developing Brain In Utero Prominently Targets Immune Cells and Promotes Early Microglial Activation. PLoS One.* 11, e0160176 (2016).

van Den Pol, A. N., Mocarski, E., Saederup, N., Vieira, J. & Meier, T. J. *Cytomegalovirus cell tropism, replication, and gene transfer in brain. J. Neurosci.* 19, 10948-10965 (1999).

Odeberg, J., et al. Human cytomegalovirus inhibits neuronal differentiation and induces apoptosis in human neural precursor cells. *J. Virol.* 80, 8929-8939 (2006).

Lazarini, F., et al. *Adult neurogenesis restores dopaminergic neuronal loss in the olfactory bulb. J. Neurosci.* 34, 14430-14442 (2014).

Khodosevich, K., et al. Connective tissue growth factor regulates interneuron survival and information processing in the olfactory bulb. *Neuron* 79, 1136-1151 (2013).

Godoy, M. D., Voegels, R. L., Pinna Fde, R., Imamura, R. & Farfel, J. M. Olfaction in neurologic and neurodegenerative diseases: a literature review. *Int. Arch. Otorhinolaryngol.* 19, 176-179. (2015).

Nalls, M. A., et al. Diagnosis of Parkinson's disease on the basis of clinical and genetic classification: a population-based modelling study. *Lancet Neurol.* 14, 1002-1009 (2015).

Braak, H. et al. Staging of the intracerebral inclusion body pathology associated with idiopathic Parkinson's disease (preclinical and clinical stages). *J. Neurol.* 249 Suppl 3, III/1-III/5 (2002).

Woolf, N. K., Koehrn, F. J., Harris, J. P. & Richman, D. D. *Congenital cytomegalovirus labyrinthitis and sensorineural hearing loss in guinea pigs. J. Infect. Dis.* 160, 929-937 (1989).

Juanjuan., C., et al. Murine model for congenital CMV infection and hearing impairment. *Virol. J.* 8, 70. (2011).

Schachtele, S. J., Mutnal, M. B., Schleiss, M. R. & Lokensgard, J. R. Cytomegalovirus-induced sensorineural hearing loss with persistent cochlear inflammation in neonatal mice. *J. Neurovirol.* 17, 201-211 (2011).

Lledo, P. M., Alonso, M. & Grubb, M. S. Adult neurogenesis and functional plasticity in neuronal circuits. *Nat. Rev. Neurosci.* 7, 179-193 (2006).

Cekinović, D., et al. *Passive immunization reduces murine cytomegalovirus-induced brain pathology in newborn mice. J Virol.* 82, 12172-12180 (2008).

Winkler, C. W., Race, B., Phillips, K. & Peterson, K. E. *Capillaries in the olfactory bulb but not the cortex are highly susceptible to virus-induced vascular leak and promote viral neuroinvasion. Acta Neuropathol.* 130, 233-245 (2015).

De Marchis, S., et al. Generation of distinct types of periglomerular olfactory bulb interneurons during development and in adult mice: implication for intrinsic properties of the subventricular zone progenitor population. *J Neurosci.* 27, 657-664 (2007).

Semple, B. D., Blomgren, K., Gimlin, K., Ferriero, D. M & Noble-Haeusslein, L. J. Brain development in rodents and humans: Identifying benchmarks of maturation and vulnerability to injury across species. *Prog. Neurobiol.* 106-107, 1-16 (2013).

Sui, Y., Horne, M. K. &, Stanić, D. Reduced proliferation in the adult mouse subventricular zone increases survival of olfactory bulb interneurons. *PLoS One* 7, e31549 (2012).

Nguyen, Y., et al. An animal model of cochlear implantation with an intracochlear fluid delivery system. *Acta oto-laryngologica* 129, 1153-1159 (2009).

Scimemi, P., Santarelli, R., Selmo, A. & Mammano, F. Auditory brainstem responses to clicks and tone bursts in C57BL/6J mice. *Acta Otorhinolaryngol. Ital.* 34, 264-271 (2014).

Lazarini, F., Gabellec, M. M., Torquet, N. & Lledo, P. M. Early activation of microglia triggers long-lasting impairment of adult neurogenesis in the olfactory bulb. *J. Neurosci.* 32, 3652-3664 (2012).

Alonso, M., et al. Activation of adult-born neurons facilitates learning and memory. *Nat. Neurosci.* 15, 897-904 (2012).

Nissant, A., Bardy, C., Katagiri, H., Murray, K. & Lledo, P. M. Neurogenesis promotes synaptic plasticity in the adult olfactory bulb. *Nat. Neurosci.* 12, 728-730 (2009).

Siopi, E., et al. *Anxiety- and Depression-Like States Lead to Pronounced Olfactory Deficits and Impaired Adult Neurogenesis in Mice. J. Neurosci.* 36, 518-31 (2016).

de Chaumont, F., et al. Icy: an open bioimage informatics platform for extended reproducible research. *Nat. Methods* 9, 690-696 (2012).

The invention claimed is:

1. A method for in vivo diagnosis of neurological impairment in a subject, whose nervous system has been infected by a neurotropic infectious agent that is CytoMegaloVirus (CMV) or is Zika virus (ZIKV), wherein said method comprises providing a kit that comprises:
   a first composition comprising odorants, wherein the odorants of said first composition consist of at least two different odorants,
   and, separately or distinctly from said first composition, a second composition comprising odorants, wherein the odorants of said second composition consist of at least two different odorants,
   and, separately or distinctly from said first composition and from said second composition,
   a third composition comprising odorants, wherein the odorants of said third composition consist of at least two different odorants,
   wherein the odorants of said second composition are the same compounds as the odorants of said third composition,
   wherein the proportion of the odorants with respect to each other in said second composition is identical to their proportion in said third composition,
   wherein the odorants of said first composition are the same compounds as the odorants of said second composition and as the odorants of said third composition,
   wherein the proportion of the odorants with respect to each other in said first composition is different from their proportion in said second composition and in said third composition, and
   wherein the subject performs sequential smelling or sniffing of the first composition, the second composition and the third composition.

2. The method of claim 1, which further comprises a step of detecting impairment of the olfactory capacity of said subject to discriminate said first composition from said second and third compositions, and wherein impairment of the olfactory capacity of said subject to discriminate said first composition from said second and third compositions is a biomarker or biological predictor of neurological impairment in said infected subject.

3. The method of claim 1, wherein said neurological impairment is:
   a. a neurodegeneration, more particularly a neurodegeneration of the Central Nervous System (CNS) and/or the Peripheral Nervous System (PNS), more particularly of the CNS, of said subject, and/or
   b. a neurological disease or disorder, more particularly a neurosensory disease or disorder and/or a neurocognitive disease or disorder.

4. The method of claim 1, wherein said neurotropic infectious agent is Human CMV (HCMV).

5. The method of claim 1, wherein said neurological impairment is or leads to at least one of
   central or peripheral neuropathies,
   hearing loss, more particularly SensoriNeural Hearing Loss (SNHL), more particularly non-genetic SNHL,
   mental retardation,
   language retardation or language disability,
   psychomotor retardation or psychomotor disability,
   visual loss, and
   Guillain-Barré syndrome.

6. The method of claim 1, wherein said subject is a human being of at least 3-year old.

7. The method of claim 1, wherein said first, second and third compositions are each separately contained in an odor dispensing device for assessing nasal chemosensory performance.

8. The method of claim 1, wherein each of said two different odorants is a monomolecular compound.

9. The method of claim 1, wherein each of said two different odorants is selected from the group consisting of the monomolecular compounds, which emit an odor or scent selected from the group consisting of anise, apple, banana, caramel, chocolate, cinnamon, clove, cocoa, coconut, coffee, cola, dill, eucalyptus, fish, flower, honey, garlic, ginger, grapefruit, grass, lavender, leather, lemon, lilac, lily of the valley, licorice, melon, mint, mushroom, onion, orange, peach, pear, peppermint, pineapple, rose, spearmint, turpentine, raspberry, sesame oil, smoked meat, soy sauce and vanilla.

10. The method of claim 1, wherein each of said two different odorants is selected from the group consisting of R-carvone, S-carvone, isoamylacetate, anethol, eugenol, 2-phenylethanol, geraniol, linalool, cineole, D-limonene, L-limonene, menthol, and cinnamon aldehyde.

11. The method of claim 1, which further comprises a step of detecting whether said subject does or not discriminate said first composition from said second and third compositions at a first point in time and whether said subject does or not discriminate said first composition from said second and third compositions at a second point in time, wherein said second point in time is different from and posterior to said first point in time, wherein at least one of said first and second points in time is in a point in time wherein said subject receives or has received a treatment against said infection and/or said neurological impairment, and wherein detecting an increase in the olfactory discrimination capacity of said subject between said first point in time and said second point in time is indicative that said treatment is therapeutically effective.

12. A method for in vivo diagnosis of neurological impairment in a subject, whose nervous system has been infected by a neurotropic infectious agent that is CytoMegaloVirus (CMV) or is Zika virus (ZIKV), wherein said method comprises having the subject perform the sequential smelling or sniffing of a first composition, of a second composition and of a third composition, wherein:
said first composition comprises odorants, wherein the odorants of said first composition consist of at least two different odorants, and
said second composition is separate or distinct from said first composition and comprises odorants, wherein the odorants of said second composition consist of at least two different odorants,
and,
said third composition is separate or distinct from said first composition and from said second composition and comprises odorants, wherein the odorants of said third composition consist of at least two different odorants,
wherein the odorants of said second composition are the same compounds as the odorants of said third composition,
wherein the proportion of the odorants with respect to each other in said second composition is identical to their proportion in said third composition,
wherein the odorants of said first composition are the same compounds as the odorants of said second composition and as the odorants of said third composition, and
wherein the proportion of the odorants with respect to each other in said first composition is different from their proportion in said second composition and in said third composition.

13. The method of claim 12, wherein said first, second and third compositions are each separately contained in an odor dispensing device for assessing nasal chemosensory performance.

14. The method of claim 12, which further comprises a step of detecting impairment of the olfactory capacity of said subject to discriminate said first composition from said second and third compositions, and wherein impairment of the olfactory capacity of said subject to discriminate said first composition from said second and third compositions is a biomarker or biological predictor of neurological impairment in said infected subject.

15. The method of claim 12, wherein said neurological impairment is a neurodegeneration, more particularly a neurodegeneration of the Central Nervous System (CNS) and/or the Peripheral Nervous System (PNS), more particularly of the CNS, of said subject.

16. The method of claim 12, wherein said neurotropic infectious agent is Human CMV (HCMV).

17. The method of claim 12, wherein said neurological impairment is or leads to at least one of
central or peripheral neuropathies,
hearing loss, more particularly SensoriNeural Hearing Loss (SNHL), more particularly non-genetic SNHL,
mental retardation,
language retardation or language disability,
psychomotor retardation or psychomotor disability,
visual loss, and
Guillain-Barré syndrome.

18. The method of claim 12, wherein said subject is a human being of at least 3-year old.

19. The method of claim 12, which further comprises a step of detecting whether said subject does or not discriminate said first composition from said second and third compositions at a first point in time and whether said subject does or not discriminate said first composition from said second and third compositions at a second point in time, wherein said second point in time is different from and posterior to said first point in time, wherein at least one of said first and second points in time is in a point in time wherein said subject receives or has received a treatment against said infection and/or said neurological impairment, and wherein detecting an increase in the olfactory discrimination capacity of said subject between said first point in time and said second point in time is indicative that said treatment is therapeutically effective.

* * * * *